(12) United States Patent  
Chen et al.

(10) Patent No.: US 8,106,227 B2
(45) Date of Patent: Jan. 31, 2012

(54) FERROCENEDIPHOSPHINES

(75) Inventors: Weiping Chen, Liverpool (GB); Felix Spindler, Starrkirch-Wil (CH); Benoît Pugin, Münchenstein (CH)

(73) Assignee: Solviasag, Basel (CH)

( * ) Notice: Subject to any disclaimer, the term of this patent is extended or adjusted under 35 U.S.C. 154(b) by 588 days.

(21) Appl. No.: 12/226,213

(22) PCT Filed: Apr. 11, 2007

(86) PCT No.: PCT/EP2007/053520
§ 371 (c)(1),
(2), (4) Date: Oct. 10, 2008

(87) PCT Pub. No.: WO2007/116081
PCT Pub. Date: Oct. 18, 2007

(65) Prior Publication Data
US 2009/0124812 A1    May 14, 2009

(30) Foreign Application Priority Data

Apr. 12, 2006  (CH) .......................... 618/06

(51) Int. Cl.
C07F 15/02 (2006.01)
(52) U.S. Cl. ........................................ 556/22
(58) Field of Classification Search ............... 556/22
See application file for complete search history.

(56) References Cited

FOREIGN PATENT DOCUMENTS

| WO | 2005/068477 | 7/2005 |
| WO | 2006/075166 | 7/2006 |
| WO | 2006/075177 | 7/2006 |
| WO | WO 2006075166 A1 * | 7/2006 |

OTHER PUBLICATIONS

International Search Report dated Jul. 17, 2007 in the International (PCT) Application PCT/EP2007/053520 of which the present application is the U.S. National Stage.
PCT Written Opinion dated Jul. 17, 2007 in the International (PCT) Application PCT/EP2007/053520 of which the present application is the U.S. National Stage.

* cited by examiner

*Primary Examiner* — Joseph Kosack
(74) *Attorney, Agent, or Firm* — Wenderoth, Lind & Ponack, L.L.P.

(57) ABSTRACT

Compounds of the formula I in the form of enantiomerically pure diastereomers or a mixture of diastereomers, (I), where the radicals $R_1$ are identical or different and are each $C_1$-$C_4$-alkyl; m is 0 or an integer from 1 to 3; n is 0 or an integer from 1 to 4; $R_2$ is a hydrocarbon radical or a C-bonded heterohydrocarbon radical; Cp is unsubstituted or $C_1$-$C_4$-alkyl-substituted cyclopentadienyl; Y is a C-bonded chiral group which directs metals of metallation reagents into the ortho position; and Phos is a P-bonded P(III) substituent. The compounds are chiral ligands for complexes of transition metals which are used as homogeneous catalysts in asymmetric syntheses.

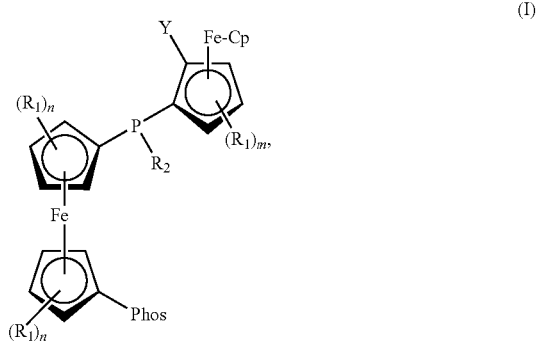

13 Claims, No Drawings

FERROCENEDIPHOSPHINES

The present invention relates to ferrocene-1,1'-diphosphines which contain a ferrocene-substituted, secondary phosphino group in the 1 position and a secondary phosphino group in the 1' position; a process for preparing them; complexes of transition metals with these ferrocenediphosphines as ligands; and the use of the metal complexes as homogeneous catalysts in stereoselective syntheses of organic compounds.

Chiral ligands have been found to be extraordinarily important auxiliaries for catalysts in homogeneous stereoselective catalysis. Metal complexes by means of which not only a sufficient catalytic activity but also a high stereoselectivity can be achieved are of practical use. Without these two properties, scale-up to industrial processes cannot be achieved for economic reasons.

The activity of such catalysts is frequently found to be specific for particular substrates. To be able to carry out optimizations for particular substrates, it is therefore necessary to have a sufficient number of chiral ligands available. There is therefore a continuing need for further efficient chiral ligands which are simple to prepare and give good results in stereoselective catalytic reactions. Ligands whose properties can be matched to particular catalytic tasks and can be optimized are of particular interest. Ligands which can be built up in a modular fashion are particularly useful here.

Ferrocene is a very useful skeleton for the preparation of ligands and has been used success-fully for providing different substitutions with secondary phosphino radicals. In addition, diphosphine ligands which have a ferrocene skeleton and contain a stereogenic P atom have become known; see, for example, C. Gambs et al., Helvetica Chimica Acta Volume 84 (2001), pages 3105 to 3126, or WO 2005/068477. However, such diphosphines have not attained any practical importance since the preparation of pure diastereomers is complicated and the diastereomers frequently tend to undergo undesirable epimerization.

It has now surprisingly been found that more stable ferrocene-1,1'-diphosphines having a stereogenic P atom are obtained when a P atom contains a ferrocenyl radical which is substituted in the ortho position relative to the bond between the cyclopentadienyl ring (Cp ring) and the P atom, in particular by substituents which contain at least one stereogenic carbon atom. In addition, it has surprisingly been found that these very modular diphosphines can be prepared in a simple fashion and can be optimized for a given catalytic problem by variation of substituents in the phosphino radicals and in the Cp ring. It has also surprisingly been found that complexes with TM8 metals are very effective, homogeneous catalysts for asymmetric syntheses, in particular for hydrogenations of α,β-unsaturated carboxylic acids, and display very high catalytic activities and stereoselectivities.

The invention firstly provides compounds of the formula I in the form of enantiomerically pure diastereomers or a mixture of diastereomers,

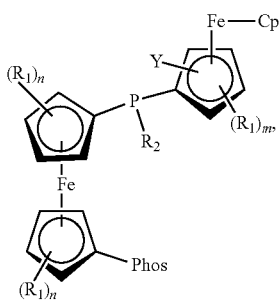

(I)

where the radicals $R_1$ are identical or different and are each $C_1$-$C_4$-alkyl;

m is 0 or an integer from 1 to 3;

n is 0 or an integer from 1 to 4;

$R_2$ is a hydrocarbon radical or a C-bonded heterohydrocarbon radical;

Cp is unsubstituted or $C_1$-$C_4$-alkyl-substituted cyclopentadienyl;

Y is a C-bonded chiral group which directs metals of metallation reagents into the ortho position; and Phos is a P-bonded P(III) substituent.

A particularly preferred P-bonded P(III) substituent Phos is a secondary phosphino group.

An alkyl group $R_1$ can be, for example, methyl, ethyl, n- or i-propyl, n-, i- or t-butyl, with preference being given to methyl. m and n are preferably 0 (and $R_1$ is thus a hydrogen atom).

The hydrocarbon radicals $R_2$ can be unsubstituted or substituted and/or contain heteroatoms selected from the group consisting of O, S, —N= or N($C_1$-$C_4$-alkyl). They can contain from 1 to 22, preferably from 1 to 18, particularly preferably from 1 to 12 and in particular from 1 to 8, carbon atoms and from 1 to 4 and preferably 1 or 2 of the heteroatoms mentioned. Radicals $R_2$ can be radicals selected from the group consisting of linear or branched $C_1$-$C_{12}$-alkyl; unsubstituted or $C_1$-$C_6$-alkyl- or $C_1$-$C_6$-alkoxy-substituted $C_4$-$C_{12}$-cycloalkyl or $C_4$-$C_{12}$-cyclo-alkyl-$CH_2$; $C_6$-$C_{14}$-aryl; $C_4$-$C_{12}$-heteroaryl; $C_{7-14}$-aralkyl; $C_4$-$C_{12}$-heteroaralkyl; or halogen- (fluorine-, chlorine- or bromine-), $C_1$-$C_6$-alkyl-, trifluoromethyl-, $C_1$-$C_6$-alkoxy-, trifluoro-methoxy-, $(C_6H_5)_3$Si—, $(C_1$-$C_{12}$-alkyl$)_3$Si— or sec-amino -substituted $C_6$-$C_{14}$-aryl, $C_4$-$C_{12}$-hetero-aryl, $C_7$-$C_{14}$-aralkyl or $C_4$-$C_{12}$-heteroaralkyl. Heteroaryl and heteroaralkyl preferably contain heteroatoms selected from the group consisting of O, S and —N=.

Examples of alkyl radicals $R_2$, which preferably contain from 1 to 6 carbon atoms, are methyl, ethyl, n-propyl, i-propyl, n-butyl, i-butyl, t-butyl and the isomers of pentyl and hexyl. Examples of unsubstituted or alkyl-substituted cycloalkyl radicals $R_2$ are cyclopentyl, cyclohexyl, methylcyclohexyl and ethylcyclohexyl, dimethylcyclohexyl, cycloheptyl, cyclooctyl, norbornyl and adamantyl. Examples of unsubstituted or alkyl- or alkoxy-substituted $C_5$-$C_{12}$-cycloalkyl-$CH_2$-radicals $R_2$ are cyclopentylmethyl, cyclohexylmethyl, cyclooctylmethyl, methylcyclohexylmethyl and dimethylcyclohexylmethyl. Examples of aryl and aralkyl radicals $R_2$ are phenyl, naphthyl, anthracenyl, fluorenyl, benzyl and naphthylmethyl. Examples of heteroaryl and heteroaralkyl radicals $R_2$ are furyl, thiophenyl, N-methylpyrrolidinyl, pyridyl, benzofuranyl, benzothiophenyl, quinolinyl, furylmethyl, thiophenylmethyl and pyridylmethyl. Examples of substituted aryl, aralkyl, heteroaryl and heteroaralkyl radicals $R_2$ are phenyl, naphthyl, benzyl, naphthylmethyl, phenylethyl, furyl, thiophenyl, benzofuryl and benzothiophenyl which are substituted by from 1 to 3 radicals selected from the group consisting of methyl, ethyl, n- and i-propyl, n-, i- and t-butyl, ethoxy, methoxy, trifluoromethyl, trifluoromethoxy, fluorine or chlorine. Some preferred examples are 2-, 3- or 4-methylphenyl, 2,4- or 3,5-dimethylphenyl, 3,4,5-trimethylphenyl, 4-ethylphenyl, 2- or 4-methylbenzyl, 2-, 3- or 4-methoxyphenyl, 2,4- or 3,5-dimethoxyphenyl, 3,4,5-trimethoxyphenyl, 2-, 3- or 4-trifluoromethylphenyl, 2,4- or 3,5-di(trifluoromethyl)phenyl, tristrifluoromethylphenyl, 2- or 4-trifluoromethoxyphenyl, 3,5-bistrifluoromethoxyphenyl, 2- or 4-fluorophenyl, 2- or 4-chlorophenyl and 3,5-dimethyl-4-methoxyphenyl.

In a particularly preferred embodiment, $R_2$ is $C_1$-$C_6$-alkyl, $C_5$-$C_8$-cycloalkyl, $C_7$-$C_8$-bicycloalkyl, o-furyl, phenyl, naphthyl, 2-($C_1$-$C_6$-alkyl)$C_6H_4$, 3-($C_1$-$C_6$-alkyl)$C_6H_4$, 4-($C_1$-$C_6$-alkyl)$C_6H_4$, 2-($C_1$-$C_6$-alkoxy)$C_6H_4$, 3-($C_1$-$C_6$-alkoxy)$C_6H_4$, 4-($C_1$-$C_6$-alkoxy)$C_6H_4$, 2-(trifluoromethyl)$C_6H_4$, 3-(trifluoromethyl)$C_6H_4$, 4-(trifluoromethyl)$C_6H_4$, 3,5-bis(trifluoromethyl)$C_6H_3$, 3,5-bis($C_1$-$C_6$-alkyl)$_2C_6H_3$, 3,5-bis($C_1$-$C_6$-alkoxy)$_2C_6H_3$ and 3,5-bis($C_1$-$C_6$-alkyl)$_2$-4-($C_1$-$C_6$-alkoxy)$C_6H_2$.

In the ortho-directing, chiral group Y, the chiral atom is preferably attached in the 1, 2 or 3 position relative to the cyclopentadienyl-Y bond. The group Y can be an open-chain or cyclic radical in which the atoms are selected from the group consisting of H, C, O, S and N.

The group Y can correspond, for example, to the formula —HC*$R_5R_6$ (where * denotes the asymmetric atom), where $R_5$ is $C_1$-$C_8$-alkyl, $C_5$-$C_8$-cycloalkyl (cyclohexyl), $C_6$-$C_{10}$-aryl (phenyl), $C_7$-$C_{12}$-aralkyl (benzyl) or $C_7$-$C_{12}$-alkaryl (methylbenzyl), $R_6$ is —$OR_7$ or —$NR_8R_9$, $R_7$ is $C_1$-$C_8$-alkyl, $C_5$-$C_8$-cycloalkyl, phenyl or benzyl and $R_8$ and $R_9$ are identical or different and are each $C_1$-$C_8$-alkyl, $C_5$-$C_8$-cycloalkyl, phenyl or benzyl or $R_8$ and $R_9$ together with the N atom form a five- to eight-membered ring. $R_5$ is preferably $C_1$-$C_4$-alkyl such as methyl, ethyl, n-propyl and phenyl. $R_7$ is preferably $C_1$-$C_4$-alkyl such as methyl, ethyl, n-propyl and n- or i-butyl. $R_8$ and $R_9$ are preferably identical radicals and are each preferably $C_1$-$C_4$-alkyl such as methyl, ethyl, n-propyl, i-propyl and n- or i-butyl or together form tetramethylene, pentamethylene or 3-oxa-1,5-pentylene. Particularly preferred groups of the formula —HC$R_5R_6$ are 1-methoxyeth-1-yl, 1-dimethylaminoeth-1-yl and 1-(dimethylamino)-1-phenylmethyl.

Y is particularly preferably a —CH$R_5$—N$R_8R_9$ group, where $R_5$ is $C_1$-$C_4$-alkyl, $C_5$-$C_6$-cycloalkyl, phenyl, $C_1$-$C_4$-alkylphenyl or $C_1$-$C_4$-alkylbenzyl, and $R_8$ and $R_9$ are identical and are each $C_1$-$C_4$-alkyl and preferably methyl or ethyl.

When Y is a radical without an asymmetric α-carbon atom, it is bound via a carbon atom either directly or via a bridging group to the cyclopentadienyl ring. The bridging group can be, for example, methylene, ethylene or an imine group. Cyclic radicals bound to the bridging group are preferably saturated and are particularly preferably $C_1$-$C_4$-alkyl-, ($C_1$-$C_4$-alkyl)$_2$NCH$_2$—, ($C_1$-$C_4$-alkyl)$_2$NCH$_2$CH$_2$—, $C_1$-$C_4$-alkoxymethyl- or $C_1$-$C_4$-alkoxyethyl-substituted N-, O- or N,O-heterocycloalkyl having a total of 5 or 6 ring atoms. Open-chain radicals are preferably bound via a CH$_2$ group to the cyclopentadienyl ring and the radicals are preferably derived from amino acids or ephedrine. Some preferred examples are:

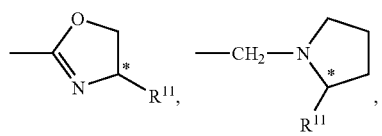

-continued

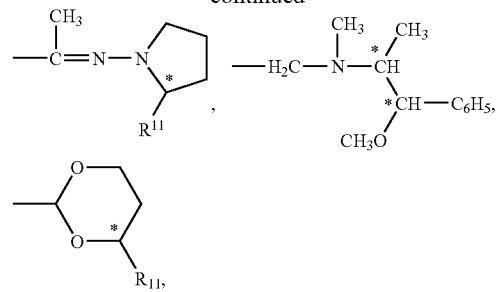

where $R_{11}$ is $C_1$-$C_4$-alkyl, ($C_1$-$C_4$-alkyl)NCH$_2$—, ($C_1$-$C_4$-alkyl)$_2$NCH$_2$CH$_2$—, $C_1$-$C_4$-alkoxymethyl or $C_1$-$C_4$-alkoxyethyl. $R_{11}$ is particularly preferably methoxymethyl or dimethylaminomethyl.

When Y is a —C*H$R_a$—O$R_b$ group, $R_a$ is preferably $C_1$-$C_4$-alkyl, $C_5$-$C_6$-cycloalkyl (cyclohexyl), phenyl, benzyl or methylbenzyl.

A P-bonded P(III) substituent Phos can be a secondary phosphino group which contains identical or different hydrocarbon radicals or in which the hydrocarbon radical together with the P atom forms a 4- to 8-membered ring. The secondary phosphino group preferably contains identical hydrocarbon radicals. The hydrocarbon radicals can be unsubstituted or substituted and/or contain heteroatoms selected from the group consisting of O, S, —N= or N($C_1$-$C_4$-alkyl). They can contain from 1 to 22, preferably from 1 to 18, particularly preferably from 1 to 12 and very particularly preferably from 1 to 8, carbon atoms and from 1 to 4, preferably 1 or 2, of the heteroatoms mentioned. The hydrocarbon radicals can be radicals selected from the group consisting of linear or branched $C_1$-$C_{12}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-CH$_2$—; $C_6$-$C_{14}$-aryl; $C_4$-$C_{12}$-heteroaryl; $C_7$-$C_{14}$-aralkyl; $C_4$-$C_{12}$-heteroaralkyl; or halogen- (fluorine-, chlorine- or bromine-), $C_1$-$C_6$-alkyl-, trifluoromethyl-, $C_1$-$C_6$-alkoxy-, trifluoromethoxy-, ($C_6H_5$)Si—, ($C_1$-$C_{12}$-alkyl)$_b$Si— or sec-amino-substituted $C_6$-$C_{14}$-aryl, $C_4$-$C_{12}$-heteroaryl, $C_7$-$C_{14}$-aralkyl or $C_4$-$C_{12}$-heteroaralkyl. Heteroaryl and heteroaralkyl preferably contain heteroatoms selected from the group consisting of O, S and —N=.

Examples of alkyl hydrocarbon radicals, which preferably contain from 1 to 6 carbon atoms, are methyl, ethyl, n-propyl, i-propyl, n-butyl, i-butyl, t-butyl and the isomers of pentyl and hexyl. Examples of unsubstituted or alkyl-substituted cycloalkyl hydrocarbon radicals are cyclopentyl, cyclohexyl, methylcyclohexyl and ethylcyclohexyl, dimethylcyclohexyl, cyclo-heptyl, cyclooctyl, norbornyl and adamantyl. Examples of unsubstituted or alkyl- or alkoxy-substituted $C_5$-$C_{12}$-cycloalkyl-CH$_2$— hydrocarbon radicals are cyclopentylmethyl, cyclohexyl-methyl, cyclooctylmethyl, methylcyclohexylmethyl and dimethylcyclohexylmethyl. Examples of aryl and aralkyl hydrocarbon radicals are phenyl, naphthyl, anthracenyl, fluorenyl, benzyl and naphthylmethyl. Examples of heteroaryl and heteroaralkyl hydrocarbon radicals are furyl, thiophenyl, N-methylpyrrolidinyl, pyridyl, benzofuranyl, benzothiophenyl, quinolinyl, furyl-methyl, thiophenylmethyl and pyridylmethyl. Examples of substituted aryl, aralkyl, heteroaryl and heteroaralkyl hydrocarbon radicals are phenyl, naphthyl, benzyl, naphthylmethyl, phenyl-ethyl, furyl, thiophenyl, benzofuryl and benzothiophenyl which are substituted by from 1 to 3 radicals selected from the group consisting of methyl, ethyl, n- and 1-propyl, n-, i- and t-butyl, ethoxy, methoxy, trifluoromethyl, trifluoromethoxy, fluorine and chlorine. Some preferred examples are 2-, 3- or 4-methylphenyl, 2,4- or 3,5-dimethylphenyl, 3,4,5-trimethylphenyl, 4-ethylphenyl, 2- or 4-methylbenzyl, 2-, 3- or 4-methoxyphenyl, 2,4- or 3,5-dimethoxyphenyl, 3,4,5-trimethoxyphenyl, 2-, 3- or 4-trifluoromethylphenyl, 2,4- or 3,5-di(trifluoromethyl)phenyl, tristrifluoromethylphenyl, 2- or 4-trifluoromethoxyphenyl, 3,5-bistrifluoromethoxyphenyl, 2- or 4-fluorophenyl, 2- or 4-chlorophenyl and 3,5-dimethyl-4-methoxyphenyl.

In a particularly preferred embodiment, the hydrocarbon radical is $C_1$-$C_6$-alkyl, $C_5$-$C_8$-cyclo-alkyl, $C_7$-$C_8$-bicycloalkyl, o-furyl, phenyl, naphthyl, 2-($C_1$-$C_6$-alkyl)$C_6H_4$, 3-($C_1$-$C_6$-alkyl)$C_6H_4$, 4-$C_1$-$C_6$-alkyl)$C_6H_4$, 2-($C_1$-$C_6$-alkoxy)$C_6H_4$, 3-($C_1$-$C_6$-alkoxy)$C_6H_4$, 4-$C_1$-$C_6$-alkoxy)$C_6H_4$, 2-(trifluoromethyl)$C_6H_4$, 3-(trifluoromethyl)$C_6H_4$, 4-(trifluoromethyl)$C_6H_4$, 3,5-bis(trifluoro-methyl)$C_6H_3$, 3,5-bis($C_1$-$C_6$-alkyl)$_2C_6H_3$, 3,5-bis($C_1$-$C_6$-alkoxy)$_2C_6H_3$ and 3,5-bis($C_1$-$C_6$-alkyl)$_2$-4-($C_1$-$C_6$-alkoxy)$C_6H_2$.

The sec-phosphino group preferably corresponds to the formula —$PR_3R_4$, where $R_3$ and $R_4$ are each, independently of one another, a hydrocarbon radical which has from 1 to 18 carbon atoms and is unsubstituted or substituted by $C_1$-$C_6$-alkyl, trifluoromethyl, $C_1$-$C_6$-alkoxy, trifluoromethoxy, ($C_1$-$C_4$-alkyl)$_2$amino, ($C_6H_5)_3$Si, ($C_1$-$C_{12}$-alkyl)Si, halogen and/or heteroatoms O.

$R_3$ and $R_4$ are preferably radicals selected from the group consisting of linear or branched $C_1$-$C_6$-alkyl, unsubstituted cyclopentyl or cyclohexyl or cyclopentyl or cyclohexyl substituted by from 1 to 3 $C_1$-$C_4$-alkyl or $C_1$-$C_4$-alkoxy radicals, furyl, unsubstituted benzyl or benzyl substituted by from one to three $C_1$-$C_4$-alkyl or $C_1$-$C_4$-alkoxy radicals and in particular unsubstituted phenyl or naphthyl or phenyl or naphthyl substituted by from one to three F, Cl, $C_1$-$C_4$-alkyl, $C_1$-$C_4$-alkoxy, $C_1$-$C_4$-fluoroalkyl or $C_1$-$C_4$-fluoroalkoxy radicals.

$R_3$ and $R_4$ are particularly preferably radicals selected from the group consisting of $C_3$-$C_8$-alkyl, cyclopentyl, cyclohexyl, furyl, naphthyl and unsubstituted phenyl or phenyl substituted by from one to three F, Cl, $C_1$-$C_4$-alkyl, $C_1$-$C_4$-alkoxy and/or $C_1$-$C_4$-fluoroalkyl.

The secondary phosphino group Phos can be a cyclic sec-phosphino group, for example a group of one of the formulae

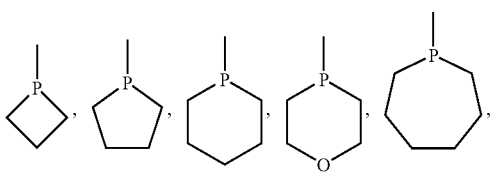

which are unsubstituted or substituted one or more times by $C_1$-$C_8$-alkyl, $C_4$-$C_8$-cycloalkyl, $C_1$-$C_6$-alkoxy, $C_1$-$C_4$-alkoxy-$C_1$-$C_4$-alkyl, phenyl, $C_1$-$C_4$-alkylphenyl or $C_1$-$C_4$-alkoxyphenyl, benzyl, $C_1$-$C_4$-alkylbenzyl or $C_1$-$C_4$-alkoxybenzyl, benzyloxy, $C_1$-$C_4$-alkylbenzyloxy or $C_1$-$C_4$-alkoxybenzyloxy or $C_1$-$C_4$-alkylidenedioxyl.

The substituents can be attached to the P atom in one or both α positions in order to introduce chiral C atoms. The substituents in one or both α positions are preferably $C_1$-$C_4$-alkyl or benzyl, for example methyl, ethyl, n- or i-propyl, benzyl or —$CH_2$—O—$C_1$-$C_4$-alkyl or —$CH_2$—O—$C_6$-$C_{10}$-aryl.

Substituents in the β,γ positions can be, for example, $C_1$-$C_4$-alkyl, $C_1$-$C_4$-alkoxy, benzyloxy or —O—$CH_2$—O—, O—CH($C_1$-$C_4$-alkyl)O— and —O—C($C_1$-$C_4$-alkyl)$_2$-O—.

Some examples are methyl, ethyl, methoxy, ethoxy, —O—CH(methyl)O— and —O—C(methyl)$_2$-O—.

Depending on the type of substitution and number of substituents, the cyclic phosphino radicals can be C-chiral, P-chiral or C- and P-chiral.

An aliphatic 5 or 6-membered ring or benzene can be fused onto two adjacent carbon atoms in the radicals of the above formulae.

The cyclic sec-phosphino radical can correspond, for example, to the formulae (only one of the possible diastereomers is shown),

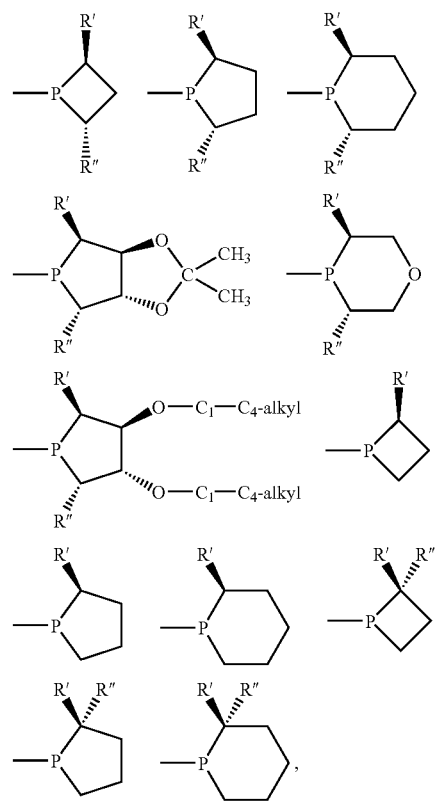

where the radicals R' and R" are each $C_1$-$C_4$-alkyl, for example methyl, ethyl, n- or i-propyl, benzyl or —$CH_2$—O—$C_1$-$C_4$-alkyl or —$CH_2$—O—$C_6$-$C_{10}$-aryl and R' and R" are identical or different.

In the compounds of the formula I, a sec-phosphino radical Phos is preferably an acyclic sec-phosphino radical selected from the group consisting of —P($C_1$-$C_6$-alkyl)$_2$, —P($C_5$-$C_8$-cycloalkyl), —P($C_{7-8}$-bicycloalkyl)$_2$, —P(o-furyl)$_2$, —P($C_6H_5$)$_2$, —P[2-($C_1$-$C_6$-alkyl)$C_6H_4$]$_2$, —P[3-($C_{1-6}$-alkyl)$C_6H_4$]$_2$, —P[4-($C_1$-$C_6$-alkyl)$C_6H_4$]$_2$, —P[2-($C_1$-$C_6$-alkoxy)$C_6H_4$]$_2$, —P[3-($C_1$-$C_6$-alkoxy)$C_6H_4$]$_2$, —P[4-($C_1$-$C_6$-alkoxy)$C_6H_4$]$_2$, —P[2-(trifluoromethyl)$C_6H_4$]$_2$, —P[3-(trifluoromethyl)$C_6H_4$]$_2$, —P[4-(tri-fluoromethyl)$C_6H_4$]$_2$, —P[3,5-bis(trifluoromethyl)$C_6H_3$]$_2$, —P[3,5-bis($C_1$-$C_6$-alkyl)$_2C_6H_3$]$_2$, —P[3,5-bis($C_1$-$C_6$-alkoxy)$_2C_6H_3$]$_2$ and —P[3,5-bis($C_1$-$C_6$-alkyl)$_2$-4-($C_1$-$C_6$-alkoxy)$C_6H_2$]$_2$ or a cyclic phosphino radical selected from the group consisting of

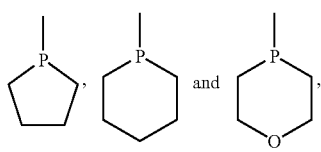

which are unsubstituted or substituted one or more times by $C_1$-$C_4$-alkyl, $C_1$-$C_4$-alkoxy, $C_1$-$C_4$-alkoxy-$C_1$-$C_2$-alkyl, phenyl, benzyl, benzyloxy or $C_1$-$C_4$-alkylidenedioxyl.

Some specific examples are —P(CH$_3$)$_2$, —P(i-C$_3$H$_7$)$_2$, —P(n-C$_4$H$_9$)$_2$, —P(i-C$_4$H$_9$)$_2$, —P(t-C$_4$H$_9$)$_2$, —P(C$_5$H$_9$), —P(C$_6$H$_{11}$)$_2$, —P(norbornyl)$_2$, —P(o-furyl)$_2$, —P(C$_6$Hs)$_2$, P[2-(methyl)C$_6$H$_4$]$_2$, P[3-(methyl)C$_6$H$_4$]$_2$, —P[4-(methyl)C$_6$H$_4$]$_2$, —P[2-(methoxy)C$_6$H$_4$]$_2$, —P[3-(methoxy)C$_6$H$_4$]$_2$, —P[4-(methoxy)C$_6$H$_4$]$_2$, —P[3-(trifluoromethyl)C$_6$H$_4$]$_2$, —P[4-(trifluoromethyl)C$_6$H$_4$]$_2$, —P[3,5-bis(trifluoromethyl)C$_6$H$_3$]$_2$, —P[3,5-bis(methyl)$_2$C$_6$H$_3$]$_2$, —P[3,5-bis(methoxy)$_2$C$_6$H$_3$]$_2$ and —P[3,5-bis(methyl)$_{24}$-(methoxy)C$_6$H$_2$]$_2$, and those of the formulae

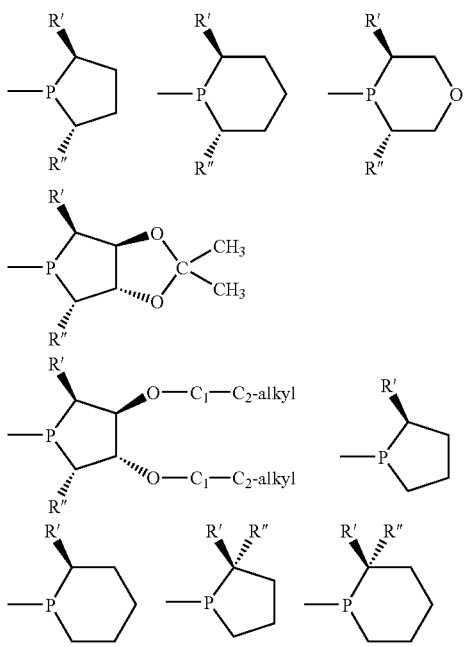

where

R' is methyl, ethyl, methoxy, ethoxy, phenoxy, benzyloxy, methoxymethyl, ethoxymethyl or benzyloxymethyl and R" independently has one of the meanings of R' but is different from R'.

The P-bonded P(III) substituent Phos can also be —PHR$_{12}$. R$_{12}$ can be one of the same hydro-carbon radicals as mentioned above for secondary phosphino groups as P-bonded P(III) substituent, including the preferences.

The P-bonded P(III) substituent Phos can also be a phosphinite radical of the formula —PR$_{13}$OR$_{14}$, where R$_{13}$ and R$_{14}$ are, independently of one another, hydrocarbon radicals as have been mentioned above for secondary phosphino groups as P-bonded P(III) substituent, including the preferences, or R$_{13}$ and R$_{14}$ together form a bivalent hydrocarbon radical which has from 3 to 8 and preferably from 3 to 6 carbon atoms in the chain and is unsubstituted or substituted by $C_1$-$C_4$-alkyl, $C_1$-$C_4$-alkoxy, $C_1$-$C_4$-alkylthio, phenoxy or ($C_1$-$C_4$-alkyl)$_3$Si—. Aromatics such as benzene or naphthalene can be fused onto the bivalent hydrocarbon radical.

The P-bonded P(III) substituent Phos can also be a phosphonite radical of the formula —POR$_{15}$OR$_{16}$, where R$_{15}$ and R$_{16}$ are, independently of one another, hydrocarbon radicals as have been mentioned above for secondary phosphino groups as P-bonded P(III) substituent, including the preferences, or R$_{15}$ and R$_{16}$ together form a bivalent hydrocarbon radical which has from 2 to 8 and preferably from 2 to 6 carbon atoms in the chain and is unsubstituted or substituted by $C_1$-$C_4$-alkyl, $C_1$-$C_4$-alkoxy, $C_1$-$C_4$-alkylthio, phenoxy or ($C_1$-$C_4$-alkyl)$_3$Si—. Aromatics such as benzene or naphthalene can be fused onto the bivalent hydrocarbon radical. When R$_{15}$ and R$_{16}$ together form a bivalent hydrocarbon radical, cyclic phosphonite groups are present.

This cyclic phosphonite group can be a five- to eight-membered ring in which the O atoms of the —O—P—O— group are bound to a $C_2$-$C_5$-chain in the α,ω positions, with the carbon chain being able to be part of a biaromatic or biheteroaromatic ring. Carbon atoms of the cyclic phosphonite group can be unsubstituted or substituted, for example by $C_1$-$C_4$-alkyl, $C_1$-$C_4$-alkoxy, halogens (F, Cl, Br), CF$_3$ and —C(O)$C_1$-$C_4$-alkyl. When the —O—P—O— group is bound to an aliphatic chain, the chain is preferably substituted or unsubstituted 1,2-ethylene or 1,3-propylene.

The cyclic phosphonite group can, for example, be formed by a substituted or unsubstituted $C_2$-$C_4$-alkylenediol, preferably $C_2$-diol, and correspond to the formula II,

where T is a direct bond or unsubstituted or substituted —CH$_2$— or —CH$_2$—CH$_2$. T is preferably a direct bond and thus forms a phosphonite radical of the formula IIa,

where R$_{100}$ is hydrogen, $C_1$-$C_4$-alkyl, phenyl, benzyl, $C_1$-$C_4$-alkoxy, or the two radicals R$_{100}$ form an unsubstituted or substituted fused-on aromatic.

Other cyclic phosphonites can, for example, be derived from 1,1'-biphenyl-2,2'-diols and correspond to the formula III or IIIa,

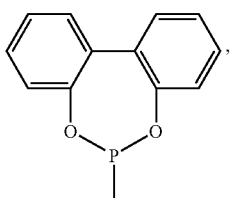

(III)

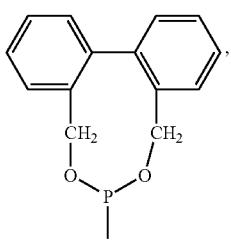

(IIIa)

where each phenyl ring is unsubstituted or substituted from one to five times, for example by halogen (F, Cl, Br), $CF_3$, $C_1$-$C_4$-alkyl, $C_{1-4}$-alkoxy or —C(O)—$C_1$-$C_4$-alkyl.

Other cyclic phosphonites can, for example, be derived from 1,1'-binaphthyl-2,2'-diols and correspond to the formula IV,

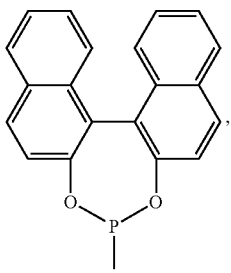

(IV)

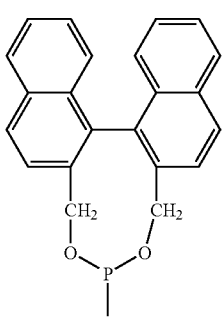

(IVa)

where each naphthyl ring is unsubstituted or substituted from one to six times, for example by halogen (F, Cl, Br), $CF_3$, $C_1$-$C_4$-alkyl, $C_1$-$C_4$-alkoxy or —C(O)$C_1$-$C_4$-alkyl.

Other cyclic phosphonites can, for example, be derived from 1,1'-biheteroaryl-2,2'-diols and correspond to the formula V,

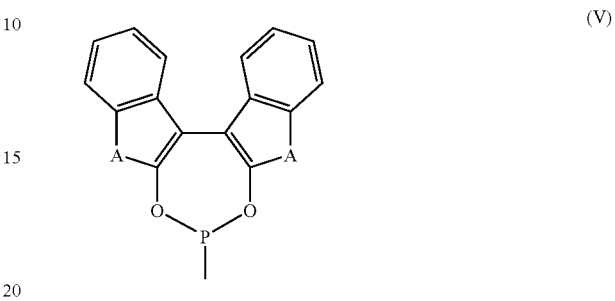

(V)

where each phenyl ring is unsubstituted or substituted from one to four times, for example by halogen (F, Cl, Br), $CF_3$, $C_1$-$C_4$-alkyl, $C_1$-$C_4$-alkoxy or —C(O)$C_1$-$C_4$-alkyl, and A is —O—, —S—, =N—, —NH— or —N$C_1$-$C_4$-alkyl-.

The P-bonded P(III) substituent Phos can also be an aminophosphino radical of the formula —P$R_{17}$N$R_{18}R_{19}$, where $R_{17}$, $R_{18}$ and $R_{19}$ are each, independently of one another, open-chain hydrocarbon radicals as have been mentioned above for secondary phosphino groups as P-bonded P(III) substituent, including the preferences, or $R_{17}$ has this meaning and $R_{18}$ and $R_{19}$ together form a bivalent hydrocarbon radical which has from 3 to 7 and preferably from 4 to 6 carbon atoms and is unsubstituted or substituted by $C_1$-$C_4$-alkyl, $C_1$-$C_4$-alkoxy, $C_1$-$C_4$-alkylthio, phenyl, benzyl, phenoxy or ($C_1$-$C_4$-alkyl)$_3$Si—.

The P-bonded P(III) substituent Phos can also be an aminophosphino radical of the formula —P(N$R_{18}R_{19}$)(N$R_{20}R_{21}$), where $R_{18}$, $R_{19}$, $R_{20}$ and $R_{21}$ have the meanings of open-chain hydro-carbon radicals $R_{17}$, including the preferences, or $R_{18}$ and $R_{19}$ together, $R_{20}$ and $R_{21}$ together or $R_{19}$ and $R_{20}$ together form a bivalent hydrocarbon radical which has from 3 to 7 and preferably from 4 to 6 carbon atoms and is unsubstituted or substituted by $C_1$-$C_4$-alkyl, $C_1$-$C_4$-alkoxy, $C_1$-$C_4$-alkylthio, phenyl, benzyl, phenoxy or ($C_1$-$C_4$-alkyl)$_3$Si—. $R_{18}$ and $R_{21}$ have the meanings given above when $R_{19}$ and $R_{20}$ together form a bivalent hydrocarbon radical.

The compounds of the formula I can be prepared in a simple and modular fashion in high yields even as enantiomerically pure diastereomers. Even intermediates can be obtained as enantiomerically pure diastereomers, which makes the preparation of pure diastereomeric end products easier. It is advantageous to start out from 1,1'-dihaloferrocene, which is commercially available, for example 1,1'-dibrormoferrocene, and in which a halogen can be selectively replaced by a metal using metallation reagents such as an alkyllithium.

In a first variant, the group $R_2$HalP— is then introduced by reaction with $R_2$—P(Hal)$_2$. Reaction with ortho-metallated and Y-substituted ferrocenes leads to a central intermediate of the formula VIII which can be obtained as pure diastereomer by heating and recrystallization:

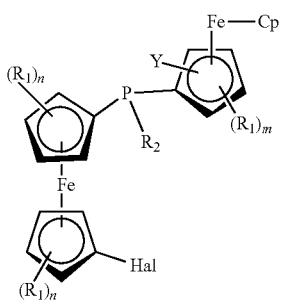

(VIII)

where Hal is halogen (Cl, Br or I, preferably Br). In the compounds of the formula VIII, a desired Phos group can be introduced after renewed metallation (replacement of Hal) by reaction with halophosphines of the formula Phos-Hal.

In another variant, the Phos group is firstly introduced by reaction with Phos-Hal and the $R_2$HalP— group is then introduced by metallation and subsequent reaction with $R_2$—P(Hal)$_2$. This gives intermediates of the formula X,

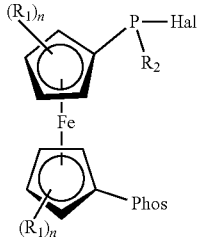

(X)

which are reacted in a final step with ortho-metallated and Y-substituted ferrocenes to give compounds of the formula I. The mixtures of diastereomers obtained can be converted into one pure diastereomer by heating and recrystallization.

The invention further provides a process for preparing compounds of the formula I, which comprises the steps:

a) metallation of a 1,1'-dihaloferrocene to give a 1-metallo-1'-haloferrocene and subsequent reaction with a compound of the formula $R_2$—P(Hal)$_2$, where Hal is chlorine, bromine or iodine, to form a compound of the formula VI,

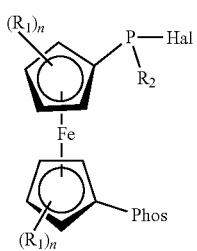

(VI)

where $R_1$, $R_2$ and n are as defined above and Hal is chlorine, bromine or iodine, b) reaction of a compound of the formula VI with a compound of the formula VII

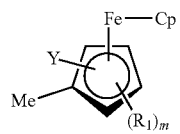

(VII)

where Y, Cp, $R_1$ and m are as defined above and M is Li or MgHal, where Hal is chlorine, bromine or iodine, to form a compound of the formula VIII,

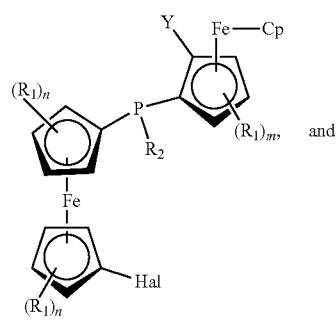

(VIII), and c) reaction of a compound of the formula VIII with an alkyllithium and then with a halophosphine of the formula Phos-Hal, where Hal is chlorine, bromine or iodine, to give a compound of the formula I.

In process step b), mixtures of diastereomers of the P-chiral compounds of the formula VIII are obtained. Mixtures of diastereomers of compounds of the formula VIII as obtained in process step b) can be separated into their various stereoisomers by means of known methods, for example chromatography.

However, these mixtures can also be converted into pure diastereomers in a surprisingly simple manner by plain thermal treatment and, if appropriate, subsequent recrystallization. Thermal treatment and, if appropriate, recrystallization is advisable before carrying out process step c) so as to avoid purification steps such as separations on chiral columns after process step c) in order to produce pure diastereomers. Thermal treatment can, for example, comprise taking up the reaction product in an inert solvent and heating it at from 40 to 150° C., preferably from 60 to 120° C., for a period of minutes to hours, for example from 10 minutes to 10 hours. Suitable solvents are mentioned below.

The dihaloferrocenes and dihalophosphines used in process step a) are either known, some of them are commercially available or they can be prepared by analogous methods. Compounds of the formula VIII are known or can be prepared by known or analogous methods. Known Y-substituted ferrocenes are used as starting materials and are metallated in the ortho position. Metallations of ferrocenes using alkyllithiums or magnesium Grignard compounds are known reactions which are described, for example, by T. Hayashi et al., Bull. Chem. Soc. Jpn. 53 (1980), pages 1138 to 1151, or in Jonathan Clayden Organolithiums: Selectivity for Synthesis (Tetrahedron Organic Chemistry Series), Pergamon Press (2002). The alkyl in the alkyllithium can, for example, contain from 1 to 6 carbon atoms and preferably from 1 to 4 carbon atoms. Methyllithium, s-butyllithium, n-butyllithium and t-butyl-lithium are frequently used. Magnesium Grignard compounds are preferably compounds of the formula ($C_1$-$C_4$-alkyl)$MgX_0$, where $X_0$ is Cl, Br or I.

The reactions in process steps a), b) and c) are advantageously carried out at low temperatures, for example from 20 to −100° C., preferably from 0 to −80° C. After addition of reagents, the temperature can also be increased, for example to room temperature. The reactions are advantageously carried out under inert protective gases, for example nitrogen or noble gases such as helium or argon.

The reactions are advantageously carried out in the presence of inert solvents. Such solvents can be used either alone or as a combination of at least two solvents. Examples of solvents are aliphatic, cycloaliphatic and aromatic hydrocarbons and also open-chain or cyclic ethers. Specific examples are petroleum ether, pentane, hexane, cyclohexane, methylcyclohexane, benzene, toluene, xylene, diethyl ether, dibutyl ether, tert-butyl methyl ether, ethylene glycol dimethyl ether or ethylene glycol diethyl ether, diethylene glycol dimethyl ether, tetrahydro-furan and dioxane.

In the reactions in process steps a), b) and c), use is made of at least equivalent amounts of the reactants or an excess of one reactant of up to 1.5 equivalents.

The invention also provides the compounds of the formula VIII in the form of enantiomerically pure diastereomers or mixtures of diastereomers,

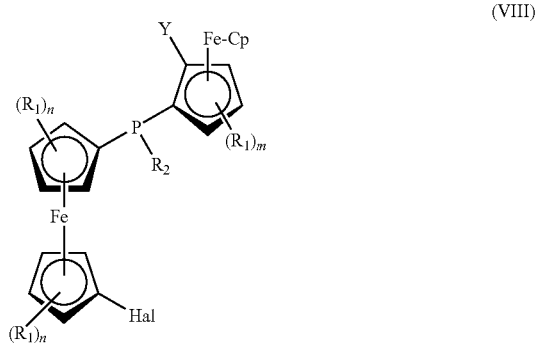

(VIII)

where the radicals $R_1$ are identical or different and are each $C_1$-$C_4$-alkyl;

m is 0 or an integer from 1 to 3;

n is 0 or an integer from 1 to 4;

$R_2$ is a hydrocarbon radical or C-bonded heterohydrocarbon radical;

Cp is unsubstituted or $C_1$-$C_4$-alkyl-substituted cyclopentadienyl;

Y is a C-bonded chiral group which directs metals of metallation reagents into the ortho position; and Hal is chlorine, bromine or iodine.

The invention further provides a process for preparing compounds of the formula I, which comprises the steps:

a) metallation of a 1,1'-dihaloferrocene to form a 1-metallo-1'-haloferrocene and subsequent reaction with a compound of the formula Phos-Hal, where halo and Hal are each chlorine, bromine or iodine, to form a compound of the formula IX

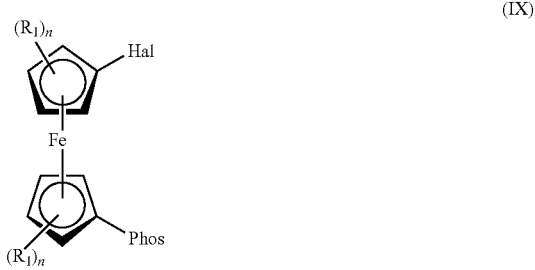

(IX)

where $R_1$, Phos and n are as defined above and Hal is chlorine, bromine or iodine, b) metallation of the compound of the formula IX and subsequent reaction with a compound of the formula $R_2$—P$(Hal)_2$ to form a compound of the formula X,

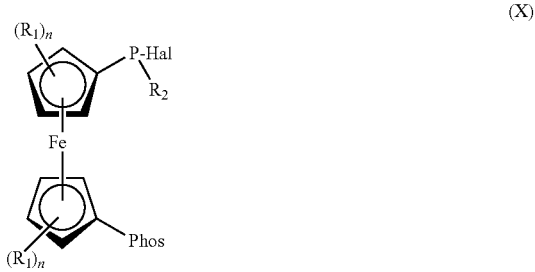

(X)

where $R_1$, $R_2$, Phos, Hal and n are as defined above, and c) reaction of a compound of the formula X with a compound of the formula VII

(VII)

to give a compound of the formula I.

In process step c), mixtures of diastereomers of the P-chiral compounds of the formula VII are obtained. Mixtures of diastereomers of compounds of the formula VII as obtained in process step c) can be separated into their various stereoisomers by means of known methods, for example chromatography.

In process step c), mixtures of diastereomers of the P-chiral compounds of the formula I are obtained. These mixtures can be converted into pure diastereomers in a surprisingly simple manner by plain thermal treatment and, if appropriate, subsequent recrystallization. Thermal treatment and, if appropriate, recrystallization is advisable for preparing pure diastereomers. Thermal treatment can, for example, comprise taking up the reaction product in an inert solvent and heating it at from 40 to 150° C., preferably from 60 to 120° C., for a period of minutes to hours, for example from 10 minutes to 10 hours. Suitable solvents are mentioned below.

The process can be carried out under analogous conditions to those of the process described first.

The invention further provides compounds of the formula Xa,

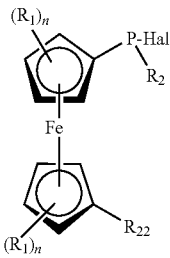

where
the radicals $R_1$ are identical or different and are each $C_1$-$C_4$-alkyl;
n is 0 or an integer from 1 to 4;
$R_2$ is a hydrocarbon radical or C-bonded heterohydrocarbon radical;
$R_{22}$ is a Phos or Hal group;
Phos is a P-bonded P(III) substituent; and
Hal is chlorine, bromine or iodine.

The compounds of the formula Xa encompass the compounds of the formula VI and the formula X.

The novel compounds of the formula I are ligands for complexes of transition metals which are excellent catalysts or catalyst precursors for asymmetric syntheses, for example the asymmetric hydrogenation of prochiral, unsaturated, organic compounds. If prochiral unsaturated organic compounds are used, a very high excess of optical isomers can be induced in the synthesis of organic compounds and a high chemical conversion can be achieved in short reaction times. The enantioselectivities and catalyst activities which can be achieved are excellent. Furthermore, such ligands can also be used in other asymmetric addition or cyclization reactions.

The invention further provides complexes of metals selected from the group of transition metals, for example TM8 metals, with one of the compounds of the formula I as ligand. For the purposes of the invention, transition metals are metals of the transition groups of the Periodic Table of the Elements.

Possible metals are, for example, Cu, Ag, Au, Ni, Co, Rh, Pd, Ir, Ru and Pt. Preferred metals are rhodium and iridium and also ruthenium, platinum and palladium.

Particularly preferred metals are ruthenium, rhodium and iridium.

The metal complexes can, depending on the oxidation number and coordination number of the metal atom, contain further ligands and/or anions. Cationic metal complexes are also possible. Such analogous metal complexes and their preparation are widely described in the literature.

The metal complexes can, for example, correspond to the general formulae XI and XII, $$A_1MeL_r \quad (XI),$$

$$(A_1MeL_r)^{(z+)}(E^-)_z \quad (XII)$$

where $A_1$ is one of the compounds of the formula I,
L represents identical or different monodentate, anionic or nonionic ligands or L represents identical or different bidentate, anionic or nonionic ligands;
r is 2, 3 or 4 when L is a monodentate ligand or r is 1 or 2 when L is a bidentate ligand;
z is 1, 2 or 3;

Me is a metal selected from the group consisting of Rh, Ir and Ru; where the metal has the oxidation states 0, 1, 2, 3 or 4;
$E^-$ is the anion of an oxo acid or complex acid; and
the anionic ligands balance the charge of the oxidation states 1, 2, 3 or 4 of the metal.

The above-described preferences and embodiments apply to the compounds of the formula I.

Monodentate nonionic ligands can, for example, be selected from the group consisting of olefins (for example ethylene, propylene), solvating solvents (nitriles, linear or cyclic ethers, unalkylated or N-alkylated amides and lactams, amines, phosphines, alcohols, carboxylic esters, sulfonic esters), nitrogen monoxide and carbon monoxide.

Suitable polydentate anionic ligands are, for example, allyls (allyl, 2-methallyl) or deprotonated 1,3-diketo compounds such as acetylacetonate.

Monodentate anionic ligands can, for example, be selected from the group consisting of halides (F, Cl, Br, I), pseudohalides (cyanide, cyanate, isocyanate) and anions of carboxylic acids, sulphonid acids and phosphonic acids (carbonate, formate, acetate, propionate, methylsulphonate, trifluoromethylsulphonate, phenylsulphonate, tosylate).

Bidentate nonionic ligands can, for example, be selected from the group consisting of linear or cyclic diolefins (for example hexadiene, cyclooctadiene, norbornadiene), dinitriles (malononitrile), unalkylated or N-alkylated carboxylic diamides, diamines, diphosphines, diols, diesters of dicarboxylic acids and diesters of disulphonic acids.

Bidentate anionic ligands can, for example, be selected from the group consisting of anions of dicarboxylic acids, disulphonic acids and diphosphonic acids (for example of oxalic acid, malonic acid, succinic acid, maleic acid, methylenedisulphonic acid and methylene-diphosphonic acid).

Preferred metal complexes also include those in which E is —Cl$^-$, —Br$^-$, —I$^-$, $ClO_4^-$, $CF_3SO_3^-$, $CH_3SO_3^-$, $HSO_4^-$, $(CF_3SO_2)_2N^-$, $(CF_3SO_2)_3C^-$, tetraarylborates such as B(phenyl)$_4^-$, B[bis(3,5-trifluoromethyl)phenyl]$_4^-$, B[bis(3,5-dimethyl)phenyl]$_4^-$, B($C_6F_5$)$_4^-$ and B(4-methylphenyl)$_4^-$, $BF_4^-$, $PF_6^-$, $SbCl_6^-$, $AsF_6^-$ or $SbF_6^-$.

Particularly preferred metal complexes which are particularly suitable for hydrogenations correspond to the formulae XIII and XIV, $$[A_1Me_2Y_1Z] \quad (XIII),$$

$$[A_1Me_2Y_1]^+E_1^- \quad (XIV)$$

where
$A_1$ is one of the compounds of the formula I;
$Me_2$ is rhodium or iridium;
$Y_1$ is two olefins or a diene;
Z is Cl, Br or I; and
$E_1^-$ is the anion of an oxo acid or complex acid.

The above-described embodiments and preferences apply to the compounds of the formula I.

An olefin ligand $Y_1$ can be a $C_2$-$C_{12}$-, preferably $C_2$-$C_6$- and particularly preferably $C_2$-$C_4$-olefin. Examples are propene, 1-butene and in particular ethylene. A diene can contain from 5 to 12 and preferably from 5 to 8 carbon atoms and can be an open-chain, cyclic or polycyclic diene. The two olefin groups of the diene are preferably connected by one or two $CH_2$ groups. Examples are 1,4-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y is preferably two ethylenes or 1,5-hexadiene, 1,5-cyclooctadiene or norbornadiene.

In formula XIII, Z is preferably Cl or Br. Examples of $E_1$ are $BF_4^-$, $ClO_4^-$, $CF_3SO_3^-$, $CH_3SO_3^-$, $HSO_4^-$, $B(phenyl)_4^-$, $B[bis(3,5-trifluoromethyl)phenyl]_4^-$, $PF_6^-$, $SbCl_6^-$, $AsF_6^-$ or $SbF_6^-$.

The metal complexes of the invention are prepared by methods known from the literature (see also U.S. Pat. Nos. 5,371,256, 5,446,844, 5,583,241 and E. Jacobsen, A. Pfaltz, H. Yamamoto (Eds.), Comprehensive Asymmetric Catalysis I to III, Springer Verlag, Berlin, 1999, and references cited therein).

The metal complexes of the invention are homogeneous catalysts, or catalyst precursors which can be activated under the reaction conditions, which can be used for asymmetric addition reactions onto prochiral, unsaturated, organic compounds.

The metal complexes can, for example, be used for asymmetric hydrogenation (addition of hydrogen) of prochiral compounds having carbon/carbon or carbon/heteroatom double bonds. Such hydrogenations using soluble homogeneous metal complexes are described, for example, in Pure and Appl. Chem., Vol. 68, No. 1, pages 131-138, (1996). Preferred unsaturated compounds to be hydrogenated contain the groups C=C, C=N and/or C=O. According to the invention, metal complexes of ruthenium, rhodium and iridium are preferably used for the hydrogenation.

The invention further provides for the use of the metal complexes of the invention as homogeneous catalysts for preparing chiral organic compounds, preferably for the asymmetric addition of hydrogen onto a carbon-carbon or carbon-heteroatom double bond in prochiral organic compounds.

The invention further provides for the use of the metal complexes of the invention as homogeneous catalysts for preparing chiral organic compounds, preferably for the asymmetric addition of hydrogen onto a carbon-carbon or carbon-heteroatom double bond in prochiral organic compounds, in the presence of acids.

A further aspect of the invention is a process for preparing chiral organic compounds by asymmetric addition of hydrogen onto a carbon-carbon or carbon-heteroatom double bond in prochiral organic compounds in the presence of a catalyst, which is characterized in that the addition reaction is carried out in the presence of catalytic amounts of at least one metal complex according to the invention.

A further aspect of the invention is the use of metal complexes in the presence of acids or the process under neutral to acidic conditions, preferably with addition of acid, in the presence of metal complexes, where the metal complexes correspond to those of WO 2006/075166 or WO 02/02578 and the embodiments and preferences described above and below otherwise apply analogously. Particular preference is given to the corresponding Rh complexes. Further particular preference is given to the metal complexes which have compounds of the general formula as described in more detail on page 4ff of WO2006/075166 and further ligand compounds described as preferred in WO2006/075166 as ligands; very particularly preferably the compound 1,1'-bis[$(S_P, R_C, S_{Fe})$(1-N,N-dimethylamino)ethylferrocenyl)phenyl-phosphino]ferrocene. Further particular preference is given to the metal complexes having compounds of the general formula (Ib) or (Ic) as described in more detail on pages 2ff of WO 02/02578 and further ligand compounds described as preferred in WO 02/02578 as ligands; very particularly preferably the compound $(R_C, R_P)$-1-{1-[bis(bis-3,5-trifluoromethyl-phenyl)phosphino]ethyl}2-(2-diphenylphosphinophenyl)ferrocene.

Preferred prochiral, unsaturated compounds to be hydrogenated can contain one or more, identical or different C=C, C=N and/or C=O groups in open-chain or cyclic organic compounds, where the C=C, C=N and/or C=O groups can be part of a ring system or be exocyclic groups. The prochiral unsaturated compounds can be alkenes, cycloalkenes, heterocycloalkenes and also open-chain or cyclic ketones, α,β-diketones, α- or β-keto-carboxylic acids and also their esters and amides, α,β-ketoacetals or -ketoketals, ketimines, kethydrazones, α-keto-β-oximes, unsaturated α,β-aminocarboxylic acids, substituted α,β-unsaturated carboxylic acids and substituted enol ethers.

Some examples of unsaturated organic compounds are acetophenone, 4-methoxy-acetophenone, 4-trifluoromethylacetophenone, 4-nitroacetophenone, 2-chloroacetophenone, corresponding unsubstituted or N-substituted acetophenonebenzylimines, unsubstituted or substituted benzocyclohexanone or benzocyclopentanone and corresponding imines, imines from the group consisting of unsubstituted or substituted tetrahydroquinoline, tetrahydro-pyridine and dihydropyrrole, and unsaturated carboxylic acids, esters, amides and salts, for example α- and, if appropriate, β-substituted acrylic acids or crotonic acids. The carboxylic acids can be acids of the formula

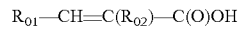

and also their salts, esters and amides, where $R_{01}$ is a substituted or unsubstituted hydrocarbon radical bound via a carbon atom and $R_{02}$ is linear or branched $C_1$-$C_{18}$-alkyl, unsubstituted or substituted $C_3$-$C_{12}$-cycloalkyl, unsubstituted or substituted $C_6$-$C_{14}$-aryloxy, unsubstituted or substituted $C_1$-$C_{18}$-alkoxy, $C_1$-$C_{18}$-hydroxyalkoxy, $C_1$-$C_{18}$-alkoxy-$C_1$-$C_6$-alkyl or protected amino (for example acetylamino).

The radicals $R_{01}$ and $R_{02}$ can be substituted one or more times by identical or different substituents, for example by unprotected or protected hydroxy, thiol or amino, CN, halogen, $C_1$-$C_6$-alkyl, $C_1$-$C_6$-haloalkyl, $C_1$-$C_6$-alkoxy, $C_1$-$C_6$-alkoxy-$C_1$-$C_4$-alkoxy, $C_6$-$C_{10}$-aryl (preferably phenyl), heteroaryl, ester groups or amide groups.

The hydrocarbon radicals $R_{01}$ can be unsubstituted or substituted and/or contain heteroatoms selected from the group consisting of O, S, —N=, —NH— or N($C_1$-$C_4$-alkyl). Aliphatic hydro-carbon radicals can contain from 1 to 30, preferably from 1 to 22, particularly preferably from 1 to 18 and very particularly preferably from 1 to 12, carbon atoms and also from 0 to 4, preferably 0, 1 or 2, of the heteroatoms mentioned. Aromatic and heteroaromatic hydro-carbon radicals can contain from 3 to 22, preferably from 3 to 18, particularly preferably from 4 to 14 and very particularly preferably from 4 to 10, carbon atoms and also from 1 to 4, preferably 1 or 2, of the heteroatoms mentioned.

Examples and preferred embodiments of hydrocarbon radicals have been given above for the radicals $R_2$ and $R_3$ and also apply to $R_{01}$ and $R_{02}$.

$R_{01}$ is preferably mononuclear or polynuclear (for example from 2 to 4 rings) $C_6$-$C_{14}$-aryl or $C_3$-$C_{14}$-heteroaryl which has heteroatoms selected from the group consisting of O, S, —N=, —NH— or N($C_1$-$C_4$-alkyl) and may be substituted, for example by unprotected or protected hydroxy, thiol or amino, $C_1$-$C_6$-alkyl, $C_1$-$C_6$-alkoxy, $C_1$-$C_6$-alkoxy-$C_1$-$C_4$-alkoxy, ester groups or amide groups. Aryl and heteroaryl: can be derived, for example, from benzene, naphthalene, indane, anthracene, phenanthrene, fluorene, thiophene, furan, pyrrole, pyridine, pyrimidine, pyrazine, benzothiophene, benzofuran, indole, isoindole and quinoline.

Some examples of unsaturated organic compounds are acetophenone, 4-methoxy-acetophenone, 4-trifluoromethylacetophenone, 4-nitroacetophenone, 2-chloroacetophenone, corresponding unsubstituted or N-substituted acetophenonebenzylimines, unsubstituted or substituted benzocyclohexanone or benzocyclopentanone and corresponding imines, imines from the group consisting of unsubstituted or substituted tetrahydroquinoline, tetrahydro-pyridine and dihydropyrrole, and unsaturated carboxylic acids, esters, amides and salts, for example α- and, if appropriate, β-substituted acrylic acids or crotonic acids. Preferred carboxylic acids are acids of the formula

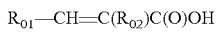

$R_{O1}-CH=C(R_{O2})C(O)OH$ and also their salts, esters and amides, where $R_{O1}$ is $C_1$-$C_6$-alkyl, unsubstituted $C_3$-$C_8$-cyclo-alkyl or $C_3$-$C_8$-cycloalkyl substituted by from 1 to 4 $C_{1-6}$-alkyl, $C_1$-$C_6$-alkoxy, $C_1$-$C_6$-alkoxy-$C_1$-$C_4$-alkoxy radicals or unsubstituted $C_6$-$C_{10}$-aryl (preferably phenyl) or heteroaryl or $C_6$-$C_{10}$-aryl (preferably phenyl) or heteroaryl substituted by from 1 to 4 $C_1$-$C_6$-alkyl, $C_1$-$C_6$-alkoxy, $C_1$-$C_6$-alkoxy-$C_1$-$C_4$-alkoxy radicals, and $R_{O2}$ is linear or branched $C_1$-$C_6$-alkyl (for example isopropyl), unsubstituted cyclopentyl, cyclohexyl or phenyl or cyclopentyl, cyclohexyl or phenyl substituted as defined above or protected amino (for example acetylamino).

It has surprisingly been found that, in the hydrogenation of carboxylic acids of the formula XV using rhodium complexes and ligands of the formula I as catalysts, quite outstanding optical yields of over 97% ee (ee equals enantiomeric excess) and, in addition, even at a high ratio of substrate to catalyst of 5000 and above, complete conversion can be achieved within short reaction times, i.e. a high catalyst activity is observed. The hydrogenation of carboxylic acids of the formula XV using metal complexes of chiral bidentate ligands is described in WO 2002/02500 A1.

A particularly preferred embodiment of the process of the invention is characterized in that compounds of the formula XV,

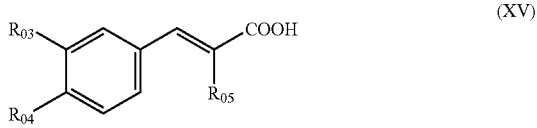

where $R_{O3}$ and $R_{O4}$ are each, independently of one another, H, $C_1$-$C_6$-alkyl, $C_1$-$C_6$-haloalkyl, $C_1$-$C_6$-alkoxy, $C_1$-$C_6$-alkoxy-$C_1$-$C_6$-alkyl or $C_1$-$C_6$-alkoxy-$C_1$-$C_6$-alkyloxy and $R_{O5}$ is $C_1$-$C_6$-alkyl, are hydrogenated by means of hydrogen in the presence of rhodium complexes having ligands of the formula I as catalysts to give compounds of the formula XVI

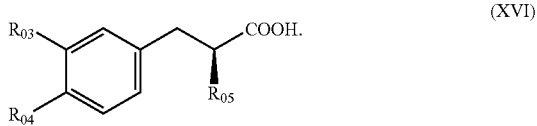

$R_{O3}$ is preferably methoxypropyloxy, $R_{O4}$ is preferably methoxy and $R_{O5}$ is preferably isopropyl.

The process of the invention can be carried out at low or elevated temperatures, for example temperatures of from −20 to 150° C., preferably from −10 to 100° C. and particularly preferably from 10 to 80° C. The optical yields are generally better at a relatively low temperature than at higher temperatures.

The process of the invention can be carried out at atmospheric pressure or superatmospheric pressure. The pressure can be, for example, from $10^5$ to $2 \times 10^7$ Pa (pascal). Hydrogenations can be carried out at atmospheric pressure or at superatmospheric pressure.

Catalysts are preferably used in amounts of from 0.0001 to 10 mol %, particularly preferably from 0.001 to 10 mol % and very particularly preferably from 0.01 to 5 mol %, based on the compound to be hydrogenated.

The preparation of the ligands and catalysts and also the hydrogenation can be carried out without a solvent or in the presence of an inert solvent, with it being possible to use one solvent or mixtures of solvents. Suitable solvents are, for example, aliphatic, cycloaliphatic and aromatic hydrocarbons (pentane, hexane, petroleum ether, cyclohexane, methylcyclohexane, benzene, toluene, xylene), aliphatic halogenated hydrocarbons (methylene chloride, chloroform, dichloroethane and tetrachloroethane), nitriles (acetonitrile, propionitrile, benzo-nitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ethyl or methyl acetate, valerolactone), N-substituted lactams (N-methylpyrrolidone), carboxamides (dimethylacetamide, dimethyl-formamide), acyclic ureas (dimethylimidazoline) and sulphoxides and sulphones (dimethyl sulphoxide, dimethyl sulphone, tetramethylene sulphoxide, tetramethylene sulphone) and alcohols (methanol, ethanol, propanol, butanol, ethylene glycol monomethyl ether, ethylene glycol monoethyl ether, diethylene glycol monomethyl ether) and water. The solvents can be used alone or as a mixture of at least two solvents.

The reaction can be carried out in the presence of cocatalysts, for example quaternary ammonium halides (tetrabutylammonium iodide), and/or in the presence of protic acids, for example mineral acids (see, for example, U.S. Pat. No. 5,583, 241 and EP-A-0 691 949). The presence of fluorinated alcohols such as 1,1,1-trifluoroethanol or of bases (amines, alkali metal hydroxides, carbonates and hydrogencarbonates) can likewise promote the catalytic reaction.

A further aspect of the invention is a process for preparing chiral organic compounds by asymmetric addition of hydrogen onto a carbon-carbon or carbon-heteroatom double bond in prochiral organic compounds in the presence of a catalyst, which is characterized in that the addition reaction is carried out in the presence of catalytic amounts of at least one metal complex according to the invention and under neutral to acidic conditions. For the purposes of the present invention, neutral to acidic conditions means the absence of basic components and particularly preferably addition of an acid.

Suitable acids are, for example:
a) organic acids: aliphatic (linear, branched or cyclic) or aromatic, unhalogenated or halogenated (fluorinated or chlorinated) carboxylic acids, sulphonic acids and phosphoric (V) adds which preferably have 1-20 carbon atoms, particularly preferably 1-12 carbon atoms, for example formic acid, acetic acid, propionic acid, n-, i-butyric acid, benzoic acid, phenyl-acetic acid, cyclohexanecarboxylic acid, chloroacetic acid, fluoroacetic acid, dichloroacetic acid and difluoroacetic acid, trichloroacetic acid and trifluoroacetic acid, perfluorobutyric acid, methanesulphonic acid, ethanesulphonic acid, benzenesulphonic acid, p-toluenesulphonic acid, chlorobenzenesulphonic acid, trifluoromethanesulphonic acid, phosphonic acids and phosphorous acids; and b) inorganic acids such as HCl (aqueous); sulphuric acid, phosphoric acid, HF, HBF$_4$, HI, HBr, solid acids such as ion exchange resins.

The acid is preferably added in an amount of 1-1 000 000 equivalents of acid per equivalent of catalyst; preferably 1-10 000 equivalents, particularly preferably 10-1000 equivalents.

In processes carried out under neutral to acidic conditions, preferably due to an addition of acid, an increase in the optical yields is surprisingly observed.

The metal complexes used as catalysts can be added as separately prepared, isolated compounds or else can be formed in situ prior to the reaction and then be mixed with the substrate to be hydrogenated. It can be advantageous to add additional ligands in the reaction using isolated metal complexes or to use an excess of ligands in the in-situ preparation. The excess can be, for example, up to 6 mol and preferably up to 2 mol, based on the metal compound used for the preparation.

The process of the invention is generally carried out by placing the catalyst in a reaction vessel and then adding the substrate, if appropriate reaction auxiliaries and the compound to be added on and subsequently starting the reaction. Gaseous compounds to be added on, for example hydrogen or ammonia, are advantageously introduced under pressure. The process can be carried out continuously or batchwise in various types of reactor.

The chiral, organic compounds according to the invention are active substances or inter-mediates for preparing such substances, in particular in the production of flavours and fragrances, pharmaceuticals and agrochemicals.

Indications given above or below in respect of a value range, for example "1-20 carbon atoms", in each case include the extreme values mentioned, i.e. one carbon atom and 20 carbon atoms.

The following examples illustrate the invention.

A) Preparation of Intermediates

All manipulations were carried out under inert gas (argon).

Abbreviations: THF=tetrahydrofuran; TBME=tert-butyl ether; n-BuLi: butyllithium; s-BuLi=sec-butyllithium; t-BuLi=tert-butyllithium; DE=diethyl ether; Hep=heptane; EA=ethyl acetate; MeOH=methanol; TMEDA=N,N,N',N'-tetramethylethylenediamine; NEt$_3$=triethylamine.

EXAMPLE A1

Preparation of (R$_C$,S$_{Fc}$,S$_P$)-1-[2-(1-dimethylaminoethyl)ferrocen-1-yl]phenyl-phosphino-1'-bromoferrocene of the formula (A1) [Ph=phenyl; Me=methyl]

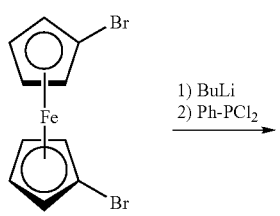

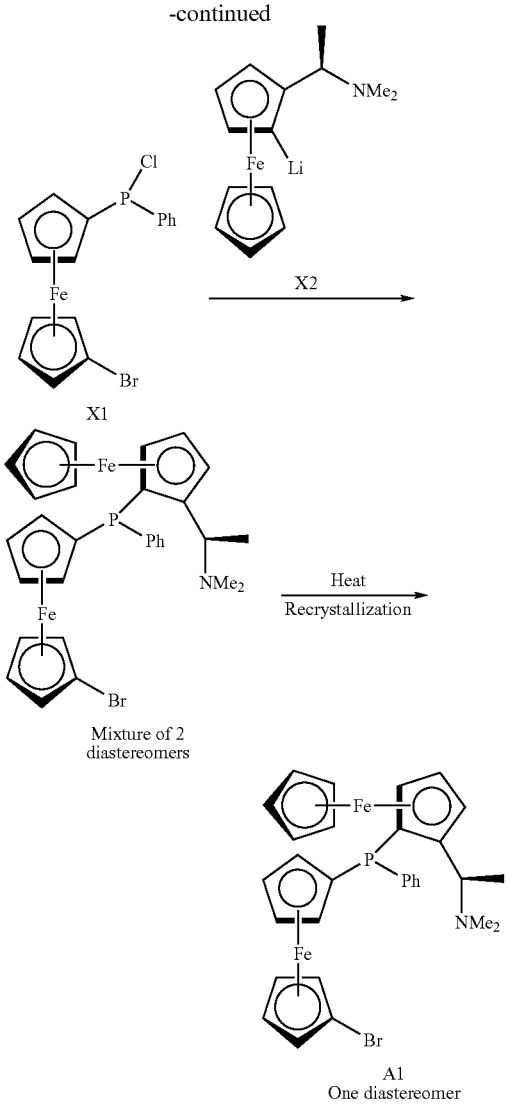

a) Preparation of 1-phenylchlorophosphine-1'-bromoferrocene (X1)

14.5 ml (23.2 mmol) of n-BuLi (1.6 M in hexane) are added dropwise to a solution of 8 g (23.2 mmol) of 1,1'-dibromoferrocene in 30 ml of THF at a temperature of <−30° C. The mixture is stirred for a further 30 minutes at this temperature. It is then cooled to −78° C. and 3.15 ml (23.2 mmol) of phenyldichlorophosphine are added dropwise at such a rate that the temperature does not exceed 60° C. After stirring the mixture at −78° C. for a further 10 minutes, the temperature is allowed to rise to room temperature and the mixture is stirred for another one hour. This gives a suspension of the monochlorophosphine X1.

b) Preparation of A1 (Mixture of Diastereomers)

15.5 ml (23.2 mmol) of t-BuLi (1.5 M in pentane) are added dropwise to a solution of 5.98 g (23.2 mmol) of (R)-1-dimethylamino-1-ferrocenylethane in 40 ml of diethyl ether (DE) at <−10° C. After stirring the mixture at the same temperature for 10 minutes, the temperature is allowed to rise to room temperature and the mixture is stirred for another 1.5 hours. This gives a solution of the compound X2 which is added via a cannula to a cooled suspension of the monochlorophosphine X1 at such a rate that the temperature does not exceed −30° C. After stirring the mixture at −30° C. for a further 10 minutes, the temperature is allowed to rise to 0° C. and the mixture is stirred for another 2 hours. The reaction mixture is admixed with 20 ml of water. The organic phase is separated off, dried over sodium sulphate and the solvent is distilled off under reduced pressure-on a rotary evaporator. Chromatographic purification (silica gel 60; eluent=heptane/ethyl acetate(EA)/NEthyl₃(Net₃) 85:10:5) gives 11.39 g of the desired product as a mixture of 2 diastereomers.

c) Preparation of A1 (One Diastereomer)

The product obtained as described in process step b) is dissolved in 50 ml of toluene and refluxed for 4 hours. After distilling off the toluene, the residue is crystallized in ethanol. This gives the compound A1 as pure diastereomer in the form of yellow crystals in a yield of 59% of theory. ¹H NMR (300 MHz, CDCl₃): δ 1.06 (d, 3H, J=6.7 Hz), 1.43 (s, 6H), 3.71 (m, 1H), 3.82 (m, 1H), 3.90 (m, 2H), 3.95 (s, 5H), 3.96 (m, 1H), 4.05 (m, 1H), 4.06 (m, 1H), 4.15 (br. s, 1H), 4.26 (m, 1H), 4.36 (m, 2H), 4.55 (m, 1H), 7.20 (m, 3H), 7.44 (m, 2H). ³¹P NMR (121.5 MHz, CDCl₃): δ −35.0 (s).

EXAMPLE A2
Preparation of 1-dicyclohexylphosphino-1'-bromoferrocene of the Formula (A2)

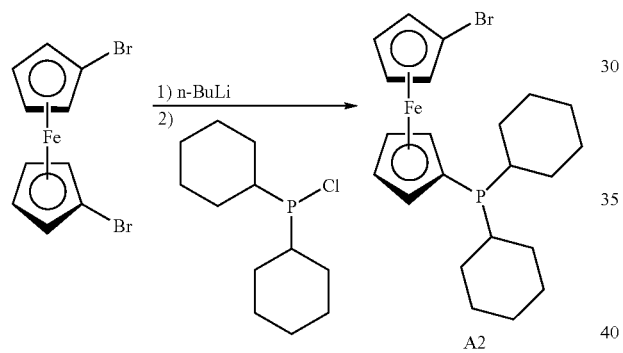

120 ml (0.3 mol) of n-BuLi (2.5 M in hexane) are added dropwise to a solution of 103 g (0.3 mol) of 1,1'-dibromoferrocene in 300 ml of THF at a temperature of <−30° C. The mixture is stirred at this temperature for a further 1.5 hours. It is then cooled to −50° C. and 66.2 ml (0.3 mol) of dicyclohexylphosphine chloride are added dropwise at such a rate that the temperature does not exceed −45° C. After stirring the mixture for a further 10 minutes, the temperature is allowed to rise to room temperature and the mixture is stirred for another one hour. After addition of 150 ml of water, the reaction mixture is shaken with hexane. The organic phases are dried over sodium sulphate and the solvent is distilled off under reduced pressure on a rotary evaporator. The residue is crystallized in ethanol. The product A2 is obtained in a yield of 84% (yellow solid). ¹H NMR (300 MHz, C₆D₆): δ 1.20-2.11 (m, 22H), 3.97 (m, 2H), 4.23 (m, 2H), 4.26 (m, 2H), 4.41 (m, 2H). ³¹P NMR (121.5 MHz, C₆D₆): δ −8.3 (s).

EXAMPLE A3
Preparation of 1,1'-ferrocenediyl)phenylphosphine of the Formula (A3)

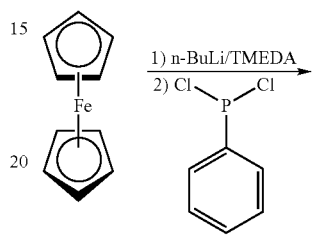

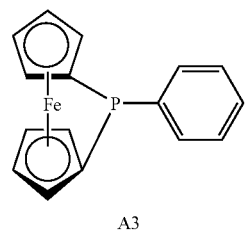

88 ml (0.22 mol) of n-BuLi (2.5 M in hexane) are added to a suspension of 18.3 g (0.1 mol) of ferrocene and 30.2 ml (0.2 mol) of TMEDA in 500 ml of hexane. The mixture is subsequently stirred at 50° C. for 2 hours. It is then cooled to −78° C. and 14.9 ml (0.11 mol) of phenyldichlorophosphine are added at such a rate that the temperature does not exceed −60° C. After the addition, the temperature is allowed to rise to room temperature and the mixture is stirred for a further one hour. 5 ml of water are then added and the mixture is filtered. The filtrate is washed with water and the organic phase is dried over sodium sulphate. The volume of the organic phase is reduced to about 100 ml by distilling off the solvent under reduced pressure on a rotary evaporator. Cooling to −30° C. gives the product A3 as red crystals (yield: 55%).

$^1$H NMR (300 MHz, C$_6$D$_6$): δ 4.29 (m, 4H), 4.40 (m, 2H), 4.64 (m, 2H), 7.23 (m, 3H), 7.71 (m, 2H). $^{31}$P NMR (121.5 MHz, C$_6$D$_6$): δ 12.9 (s).

B) Preparation of Diphosphines

EXAMPLES B1-B14

Preparation of the Diphosphine Compounds of the Formula B1 to B14 from (R$_C$,S$_{Fc}$,S$_P$)-1-[2-(1-dimethylaminoethyl)ferrocen-1-yl]phenylphosphino-1'-bromoferrocene of the Formula (A1)

General synthesis scheme:

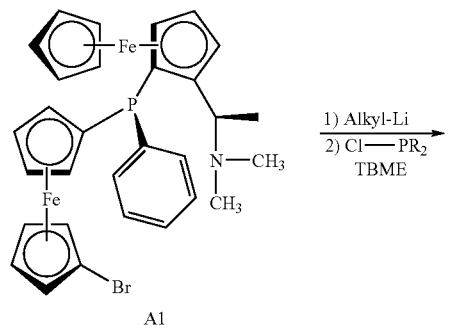

A1

1) Alkyl-Li
2) Cl—PR$_2$
TBME

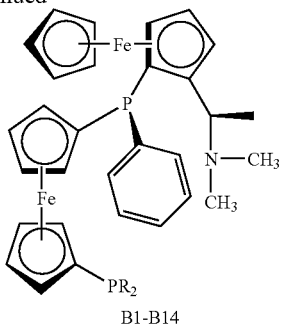

B1-B14

B1  R = cyclohexyl
B2  R = tert-butyl
B3  R = phenyl
B4  R = 3,5-di(trifluoromethyl)phenyl
B5  R = 3,5-dimethylphenyl
B6  R = 3,5-dimethyl-4-methoxyphenyl
B7  R = 1-naphtyl
B8  R = 2-bornyl
B9  R = 4-fluorophenyl
B10 R = 2-methoxyphenyl
B11 R = 4-trifluoromethylphenyl
B12 R = 2-furyl
B13 R = ethyl
B14 R = isopropyl General synthetic method for the preparation of the compounds B1-B14. Specific details regarding the respective examples are summarized in the following table:

1.1 mmol of n-BuLi (1.6 M in hexane) or s-BuLi (1.3 M in cyclohexane) are added dropwise to a solution of 1 mmol of the compound A1 in from 3 to 5 ml of tert-butyl methyl ether (TBME) at a temperature of from −5° C. to 0° C. The temperature is maintained at 0° C., the mixture is stirred for a further one hour and 1.1 mmol of the chlorophosphine ClPR$_2$ are then added. The temperature is allowed to rise to room temperature, the reaction mixture is stirred for a further one hour and is then admixed with 5 ml of a saturated aqueous NaHCO$_3$ solution. The organic phase is separated off, dried over sodium sulphate and the solvent is distilled off under reduced pressure on a rotary evaporator. Chromatographic purification (silica gel 60; eluent=see table) and, if required, crystallization in methanol gives the compounds B1-B14 as pure diastereomers.

| Example | Alkyl-lithium | Cl-PR$_2$ R: | Chromatography, Eluent | Crystallization | Yield | Appearance | Comment |
|---|---|---|---|---|---|---|---|
| B1 | s-BuLi | Cyclohexyl | Hep/EA/NEt3 85:10:5 | in MeOH | 95% | orange solid | |
| B2 | s-BuLi | tert-Butyl | Purification not necessary | — | Quantitative | orange solid | (a) |
| B3 | n-BuLi | Phenyl | Hep/EA/NEt$_3$ 80:15:5 | in MeOH | 82% | orange solid | |
| B4 | n-BuLi | 3,5-Di(trifluoromethyl)phenyl | Hep/EA/NEt$_3$ 80:15:5 | in MeOH | 86% | orange solid | |
| B5 | n-BuLi | 3,5-Dimethylphenyl | Hep/EA/NEt$_3$ 80:15:5 | in MeOH | 48% | orange solid | |
| B6 | n-BuLi | 3,5-Dimethyl-4-methoxyphenyl | Hep/EA/NEt$_3$ 80:15:5 | in MeOH | 92% | orange solid | |
| B7 | n-BuLi | 1-Naphthyl | Hep/EA/NEt$_3$ 85:10:5 | in MeOH | 88% | orange solid | |
| B8 | n-BuLi | 2-Bornyl | Hep/EA/NEt$_3$ 80:15:5 | in MeOH | 89% | orange solid | (b) |
| B9 | n-BuLi | 4-Fluorophenyl | Hep/EA/NEt$_3$ 80:15:5 | in MeOH | 93% | orange solid | |
| B10 | n-BuLi | 2-Methoxyphenyl | Hep/EA/NEt$_3$ 80:15:5 | in MeOH | 23% | orange solid | |
| B11 | n-BuLi | 4-Trifluoromethylphenyl | Hep/EA/NEt$_3$ 80:15:5 | in MeOH | 54% | orange solid | |
| B12 | n-BuLi | 2-Furyl | Hep/EA/NEt$_3$ 80:15:5 | in MeOH | 83% | orange solid | |

-continued

| Example | Alkyl-lithium | Cl-PR₂ R: | Chromatography, Eluent | Crystal-lization | Yield | Appear-ance | Comment |
|---|---|---|---|---|---|---|---|
| B13 | s-BuLi | Ethyl | Hex/EA 5:1 1% NEt₃ | in MeOH | 91% | orange oil | |
| B14 | s-BuLi | Isopropyl | Hex/EA 5:1 1% NEt₃ | in MeOH | 95% | orange oil | |

(a) After addition of di-t-butylphosphine chloride, the reaction mixture is additionally stirred at 50° C. for one hour before addition of the NaHCO₃ solution.
(b) The bis(2-bornyl)phosphine chloride is used as a mixture of various diastereomers.

NMR data for the compounds B1 to B14:

Compound B1

($R_C,S_{Fc},S_P$)-1-[2-(1-dimethylaminoethyl)ferrocen-1-yl]phenylphosphino-1'-dicyclohexylphosphinoferrocene (B1)

$^1$H NMR (300 MHz, C₆D₆): δ 1.15 (d, 3H, J=6.7 Hz), 1.77 (s, 6H), 1.25-2.28 (m, 22H), 4.01 (m, 1H), 4.05 (m, 1H), 4.10 (m, 1H), 4.11 (m, 1H), 4.14 (s, 5H), 4.20 (br. s, 1H), 4.26 (m, 2H), 4.36 (m, 1H), 4.37 (m, 1H), 4.49 (m, 2H), 4.75 (m, 1H), 7.24 (m, 3H), 7.80 (m, 2H). $^{31}$P NMR (121.5 MHz, C₆D₆): δ −35.6 (s); −7.5 (s).

Compound B2

($R_C,S_{Fc},S_P$)-1-[2-(1-dimethylaminoethyl)ferrocen-1-yl]phenylphosphino-1'-di-tert-butylphosphinoferrocene (B2)

$^1$H NMR (300 MHz, CDCl₃): δ 1.07 (s, 3H), 1.11 (s, 6H), 1.14 (d, 3H, J=6.6 Hz), 1.15 (s, 3H), 1.20 (s, 3H), 1.25 (s, 3H), 1.50 (s, 6H), 3.72 (m, 1H), 3.86 (m, 2H), 4.02 (s, 5H), 4.03 (m, 1H), 4.12 (m, 3H), 4.21 (m, 1H), 4.30 (m, 2H), 4.40 (m, 1H), 4.56 (m, 1H), 7.27 (m, 3H), 7.53 (m, 2H). $^{31}$P NMR (121.5 MHz, CDCl₃): δ −35.0 (s), 28.4 (s).

Compound B3

($R_C,S_{Fc},S_P$)-1-[2-(1-dimethylaminoethyl)ferrocen-1-yl]phenylphosphino-1'-diphenylphosphinoferrocene (B3)

$^1$H NMR (300 MHz, CDCl₃): δ 1.12 (d, 3H, J=6.6 Hz), 1.48 (s, 6H), 3.57 (m, 1H), 3.69 (m, 1H), 3.83 (m, 1H), 4.00 (s, 5H), 4.02 (m, 1H), 4.10 (m, 3H), 4.20 (br. s, 1H), 4.25 (m, 1H), 4.29 (m, 1H), 4.31 (m, 1H), 4.52 (m, 1H), 7.18~7.46 (m, 15H). $^{31}$P NMR (121.5 MHz, CDCl₃): δ −35.2 (s), −16.1 (s).

Compound B4

($R_C,S_{Fc},S_P$)-1-[2-(1-dimethylaminoethyl)ferrocen-1-yl]phenylphosphino-1'-bis-[3,5-di(trifluoromethyl)phenyl]phosphinoferrocene (B4)

$^1$H NMR (300 MHz, CDCl₃): δ 1.10 (d, 3H, J=6.6 Hz), 1.45 (s, 6H), 3.38 (m, 1H), 3.75 (m, 1H), 3.81 (m, 1H), 4.00 (s, 5H), 4.10 (m, 1H), 4.13 (m, 1H), 4.19 (m, 2H), 4.21 (m, 1H), 4.27 (m, 1H), 4.34 (m, 1H), 4.41 (m, 1H), 4.58 (m, 1H), 7.17 (m, 3H), 7.38 (m, 2H), 7.66 (t, 4H, J=7.0 Hz), 7.86 (s, 2H). $^{31}$P NMR (121.5 MHz, CDCl₃): δ −35.7 (s), −13.5 (s).

Compound B5

($R_C,S_{Fc},S_P$)-1-[2-(1-dimethylaminoethyl)ferrocen-1-yl]phenylphosphino-1'-bis-(3,5-dimethylphenyl)phosphinoferrocene (B5)

$^1$H NMR (300 MHz, CDCl₃): δ 1.48 (d, 3H, J=6.6 Hz), 2.26 (s, 6H), 3.57 (m, 1H), 3.75 (m, 1H), 3.84 (m, 1H), 3.97 (m, 1H), 4.01 (s, 5H), 4.13 (m, 4H), 4.22 (m, 2H), 4.25 (m, 1H), 4.32 (m, 1H), 4.51 (m, 1H), 6.88 (s, 1H), 6.91 (s, 2H), 6.93 (s, 2H), 6.95 (s, 1H), 7.19 (m, 3H), 7.44 (m, 2H). $^{31}$P NMR (121.5 MHz, CDCl₃): δ −35.1 (s), −16.1 (s).

Compound B6

($R_C,S_{Fc},S_P$)-1-[2-(1-dimethylaminoethyl)ferrocen-1-yl]phenylphosphino-1'-bis-(3,5-dimethyl-4-methoxyphenyl)phosphinoferrocene (B6)

$^1$H NMR (300 MHz, CDCl₃): δ 1.49 (d, 3H, J=6.6 Hz), 2.23 (s, 6H), 3.55 (br. s, 1H), 3.71 (s, 3H), 3.72 (s, 3H), 3.85 (m, 1H), 3.95 (m, 1H), 4.01 (s, 5H), 4.14 (m, 4H), 4.21 (m, 2H), 4.25 (m, 1H), 4.32 (m, 1H), 4.53 (m, 1H), 6.90 (s, 1H), 6.93 (s, 1H), 6.95 (s, 1H), 6.98 (s, 1H), 7.21 (m, 3H), 7.44 (m, 2H). $^{31}$P NMR (121.5 MHz, CDCl₃): δ 35.1 (s), −18.3 (s).

Compound B7

($R_C,S_{Fc},S_P$)-1-[2-(1-dimethylaminoethyl)ferrocen-1-yl]phenylphosphino-1'-di(1-naphthyl)phosphinoferrocene (B7)

$^1$H NMR (300 MHz, CDCl₃): δ 1.10 (d, 3H, J=6.6 Hz), 1.45 (s, 6H), 3.53 (m, 1H), 3.62 (m, 1H), 3.72 (br. s, 1H), 3.79 (br. s, 1H), 3.94 (s, 5H), 3.95 (m, 1H), 4.02 (m, 2H), 4.05 (br. s, 1H), 4.17 (br. s, 1H), 4.26 (br. s, 1H), 4.31 (m, 1H), 4.41 (m, 1H), 7.15-7.24 (m, 5H), 7.31-7.56 (m, 8H), 7.82 (m, 4H), 8.54 (m, 1H), 8.99 (dd, 1H, J=8.1 and 5.4 Hz). $^{31}$P NMR (121.5 MHz, CDCl₃): A40.4 (s), −35.3 (s).

EXAMPLE B8

($R_C,S_{Fc},S_P$)-1-[2-(1-dimethylaminoethyl)ferrocen-1-yl]phenylphosphino-1'-di(2-bornyl)phosphinoferrocene (B8)

The product is obtained as a mixture of 4 diastereomers. $^{31}$P NMR (121.5 MHz, C₆D₆): δ −35.6 (s), −35.4 (s), −35.3 (s), −35.1 (s); −13.8 (s), −11.3 (s), −10.8 (s), −10.1 (s).

EXAMPLE B9

($R_C,S_{Fc},S_P$)-1-[2-(1-dimethylaminoethyl)ferrocen-1-yl]phenylphosphino-1'-di(4-fluorophenyl)phosphinoferrocene (B9)

$^1$H NMR (300 MHz, CDCl$_3$): δ 1.14 (d, 3H, J=6.6 Hz), 1.50 (s, 6H), 3.47 (br. s, 1H), 3.68 (br. s, 1H), 3.84 (m, 1H), 4.02 (s, 5H), 4.12 (m, 3H), 4.20 (br. s, 1H), 4.23 (m, 2H), 4.32 (m, 1H), 4.35 (m, 1H), 4.56 (m, 1H), 6.97 (d, 2H, J=8.7 Hz), 7.02 (d, 2H, J=8.7 Hz), 7.25 (m, 7H), 7.43 (m, 2H). $^{31}$P NMR (121.5 MHz, CDCl$_3$): δ −35.3 (s); −18.5 (s).

EXAMPLE B10

($R_C,S_{Fc},S_P$)-1-[2-(1-dimethylaminoethyl)ferrocen-1-yl]phenylphosphino-1'-di(2-methoxyphenyl)phosphinoferrocene (B10)

$^1$H NMR (300 MHz, C$_6$D$_6$): δ 1.17 (d, 3H, J=6.7 Hz), 1.76 (s, 6H), 3.39 (s, 3H), 3.52 (s, 3H), 3.90 (br. s, 1H), 3.94 (br. s, 1H), 4.10 (m, 2H), 4.13 (s, 5H), 4.19 (br. s, 1H), 4.31 (br. s, 1H), 4.35 (m, 3H), 4.54 (m, 1H), 4.58 (br. s, 1H), 4.93 (br. s, 1H), 6.62 (dd, 2H, J=12.2 and 7.0 Hz), 6.81 (t, 1H, J=7.3 Hz), 6.90 (t, 1H, J=7.3 Hz), 7.19 (m, 3H), 7.38 (t, 2H, J=5.9 Hz), 7.69 (m, 2H). $^{31}$P NMR (121.5 MHz, C$_6$D$_6$): δ 42.6 (s); −35.6 (s).

EXAMPLE B11

($R_C,S_{Fc},S_P$)-1-[2-(1-dimethylaminoethylferrocen-1-yl]phenylphosphino-1'-di(4-trifluoromethylphenyl)phosphinoferrocene (B11)

$^1$H NMR (300 MHz, CDCl$_3$): δ 1.04 (d, 3H, J=6.7 Hz), 1.40 (s, 6H), 3.42 (br. s, 1H), 3.57 (br. s, 1H), 3.73 (br. s, 1H), 3.93 (s, 5H), 4.04 (m, 2H), 4.08 (br. s, 1H), 4.11 (br. s, 1H), 4.14 (br. s, 1H), 4.17 (m, 1H), 4.26 (m, 2H), 4.48 (m, 1H), 7.11-7.48 (m, 13H). $^{31}$P NMR (121.5 MHz, CDCl$_3$): δ −35.6 (s); −15.5 (s).

EXAMPLE B12

($R_C,S_{Fc},S_P$)-1-[2-(1-dimethylaminoethyl)ferrocen-1-yl]phenylphosphino-1'-di(2-furyl)phosphinoferrocene (B12)

$^1$H NMR (300 MHz, C$_6$D$_6$): δ 1.15 (d, 3H, J=6.7 Hz), 1.74 (s, 6H), 3.14 (br. s, 1H), 3.85 (br. s, 1H), 4.05 (br. s, 1H), 4.09 (m, 1H), 4.11 (s, 5H), 4.20 (br. s, 3H), 4.30 (br. S, 1H), 4.34 (br. s, 1H), 4.36 (m, 1H), 4.41 (br. s, 1H), 4.66 (m, 1H), 4.78 (m, 1H), 6.12 (m, 2H), 6.74 (br. s, 1H), 6.77 (br. s, 1H), 7.19 (m, 3H), 7.30 (s, 1H), 7.35 (s, 1H), 7.60 (m, 2H). $^{31}$P NMR (121.5 MHz, C$_6$D$_6$): −64.2 (s); −35.4 (s).

EXAMPLE B13

($R_C,S_{Fc},S_P$)-1-[2-(1-dimethylaminoethyl)ferrocen-1-yl]phenylphosphino-1'-diethylphosphinoferrocene (B13)

$^1$H NMR (300 MHz, C$_6$D$_6$): δ 1.09-1.22 (m, 9H), 1.56 (m, 2H), 1.69 (m, 2H), 1.76 (s, 6H), 4.01 (m, 1H), 4.06 (m, 1H), 4.11 (m, 2H), 4.13 (s, 5H), 4.19 (m, 2H), 4.29 (m, 1H), 4.36 (m, 1H), 4.38 (m, 1H), 4.45 (m, 2H), 4.77 (m, 1H), 7.22 (m, 3H), 7.78 (m, 2H). $^{31}$P NMR (121.5 MHz, C$_6$D$_6$): δ −35.0 (s); −26.5 (s).

EXAMPLE B14

($R_C,S_{Fc},S_P$)-1-[2-(1-dimethylaminoethyl)ferrocen-1-yl]phenylphosphino-1'-diiosopropylphosphinoferrocene (B14)

$^1$H NMR (300 MHz, C$_6$D$_6$): δ 1.23-1.26 (m, 15H), 1.76 (s, 6H), 1.90 (m, 1H), 2.00 (m, 1H), 3.97 (m, 1H), 4.05 (m, 1H), 4.11 (m, 2H), 4.14 (s, 5H), 4.19 (m, 1H), 4.22 (m, 1H), 4.29 (m, 1H), 4.36 (m, 1H), 4.38 (m, 2H), 4.43 (m, 1H), 4.47 (m, 1H), 4.76 (m, 1H), 7.19 (m, 3H), 7.79 (m, 2H). $^{31}$P NMR (121.5 MHz, C$_6$D$_6$): δ −35.6 (s); −0.0 (s).

EXAMPLE B15-B16

Preparation of the Diphosphine Compounds of the Formulae B15 and B16 from 1-dicyclohexylphosphino-1'-bromoferrocene of the Formula (A2)

General synthesis scheme:

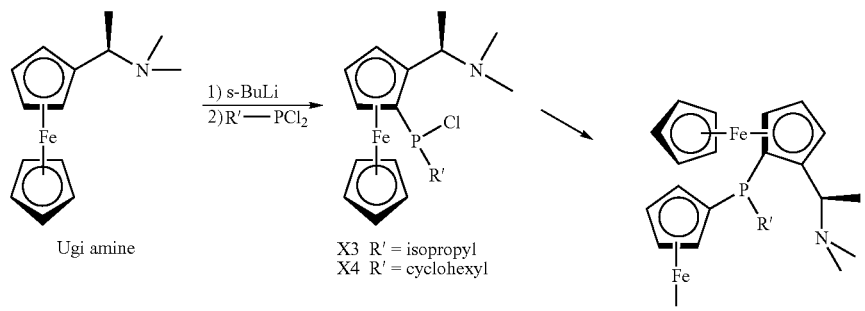

Ugi amine

X3 R' = isopropyl
X4 R' = cyclohexyl

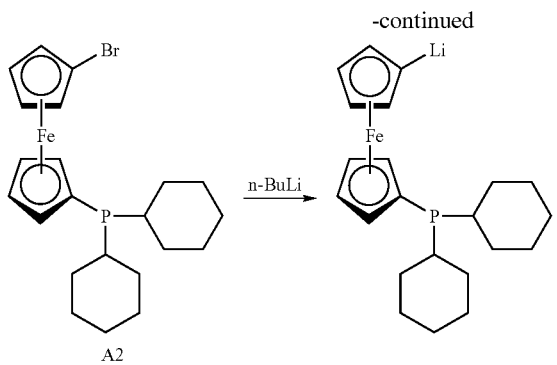
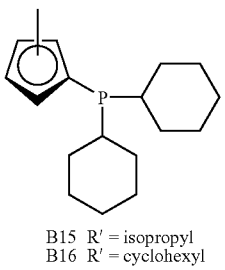

B15 R' = isopropyl
B16 R' = cyclohexyl

EXAMPLE B15

Preparation of the Two Diastereomers $(R_C,S_{Fc},R_P)$-1-[2-(1-dimethylaminoethyl) ferrocen-1-yl]isopropylphosphino-1'-dicyclohexylphosphinoferrocene of the Formula (B15a)

and $(R_C,S_{Fc},S_P)$-1-[2-(1-dimethylaminoethyl)ferrocen-1-yl] isopropylphosphino-1'-dicyclohexylphosphinoferrocene of the formula (B15b)

a) Preparation of the Chlorophosphine (X3)

3.85 ml (5 mmol) of s-BuLi (1.3 M in cyclohexane) are added dropwise to a solution of 1.29 g (5 mmol) of (R)-1-dimethylamino-1-ferrocenylethane in 5 ml of TBME at <−20° C. After stirring the mixture at the same temperature for 10 minutes, the temperature is allowed to rise to room temperature and the mixture is stirred for another 1.5 hours. The reaction mixture is then cooled to −78° C. and 0.62 ml (5 mmol) of dichloroisopropylphosphine is added dropwise at such a rate that the temperature does not exceed −60° C. Further stirring at −78° C. for 30 minutes and subsequently at room temperature for one hour gives a suspension comprising the chlorophosphine X3.

b) Preparation of the Compound B15a and B15b (Two Diastereomers):

In another reaction vessel, 3.31 ml (5 mmol) of n-BuLi (1.6 M in hexane) are added dropwise to 2.31 g (5 mmol) of the compound A2 in 10 ml of TBME at <−60° C. After the addition, the temperature is allowed to rise to 0° C. and the mixture is stirred at this temperature for another 30 minutes. The resulting reaction solution is then added to the cooled suspension of the chlorophosphine X3, with care being taken to ensure that the temperature does not exceed −50° C. After the addition, the temperature is allowed to rise to room temperature and the mixture is stirred for another 1.5 hours. After addition of 5 ml of saturated, aqueous $NaHCO_3$ solution, the reaction mixture is extracted. The organic phase is dried over sodium sulphate and the solvent is distilled off under reduced pressure on a rotary evaporator. This gives a mixture of the two diastereomers $(R_C,S_{Fc},R_P)$-B15a/$(R_C,S_{Fc},S_P)$-B15b in a ratio of about 9:1, which can be separated by column chromatography (silica gel 60; eluent=firstly hexane/EA 8:1, then additionally 1% of triethylamine). The first fraction gives the diastereomer $(R_C,S_{Fc},S_P)$-B15b (0.35 g; yield=9.8%, orange solid), and the second fraction gives the diastereomer $(R_C,S_{Fc},R_P)$-B15a (2.78 g; yield=78%, orange solid).

Diastereomer $(R_C,S_{Fc},R_P)$-B15a: $^1$H NMR (300 MHz, $C_6D_6$): δ 0.94~2.31 (m, 22H), 1.10 (d, 3H, J=6.7 Hz), 1.19 (dd, 3H, J=13.7 and 7.0 Hz), 1.63 (dd, 3H, J=15.0 and 7.0 Hz), 2.12 (s, 6H), 2.80 (m, 1H), 3.37 (q, 1H, J=6.7 Hz), 4.16 (m, 1H), 4.20 (m, 1H), 4.23 (s, 5H), 4.35 (m, 1H), 4.40 (m, 2H), 4.44 (m, 1H), 4.46 (m, 2H), 4.48 (m, 1H), 4.52 (m, 1H), 4.80 (m, 1H). $^{31}$P NMR (121.5 MHz, C6D6): δ −16.4 (s), −7.8 (s).

Diastereomer $(R_C,S_{Fc},S_P)$-B15b: $^1$H NMR (300 MHz, $C_6D_6$): δ 0.90~2.17 (m, 35H), 2.25 (s, 6H), 2.39 (m, 1H), 2.92 (m, 1H, J=6.6 Hz), 3.93 (m, 1H), 4.07 (s, 5H), 4.21 (m, 1H), 4.27 (m, 1H), 4.38 (m, 3H), 4.43 (m, 4H), 4.47 (m, 1H), 4.74 (m, 1H). $^{31}$P NMR (121.5 MHz, $C_6D_6$): δ −24.4 (s), −7.8 (s).

c) Thermal Epimerization of the Diastereomer $(R_C,S_{Fc},R_P)$-B15a:

1 g of the diastereomer $(R_C,S_{Fc},R_P)$-B15a is heated without addition of solvent or diluent at 150° C. for two hours. After cooling and chromatographic purification (same conditions as in section b), 0.65 g of the diastereomer $(R_C,S_{Fc},S_P)$-B15b and 0.15 g of the diastereomer $(R_C,S_{Fc},R_P)$-B15a are isolated.

EXAMPLE B16

Preparation of the Two Diastereomers $(R_C,S_{Fc},R_P)$-1-[2-(1-dimethylaminoethyl)-ferrocen-1-yl]cyclohexylphosphino-1'-dicyclohexylphosphinoferrocene of the Formula (16a) and $(R_C,S_{Fc},S_P)$-1-[2-(1-dimethylaminoethyl)ferrocen-1-yl]cyclohexylphosphino-1'-dicyclohexylphosphinoferrocene of the Formula (B16b)

The preparation of the two diastereomers B16a and B16b is carried out in a manner analogous to Example B15, with the difference that the chlorophosphine X4 is prepared by use of dichlorohexylphosphine instead of dichloroisopropylphosphine and this chlorophosphine X4 is reacted further.

The reaction gives a mixture of the two diastereomers $(R_C,S_{Fc},R_P)$-B16a/$(R_C,S_{Fc},S_P)$-B16b in a ratio of about 1:1. This crude product is epimerized by heating to 150° C. for 1.5 hours and subsequently purified by column chromatography (silica gel 60; eluent=firstly hexane/EA 10:1, then additionally 1% of triethylamine). The first fraction gives the diastereomer $(R_C,S_{Fc},S_P)$-B16b (yield=40%, orange solid), and the second fraction gives the diastereomer $(R_C,S_{Fc},R_P)$-B15a (yield=10%, orange solid).

$(R_C,S_{Fc},R_P)$-B16a: $^1$H NMR (300 MHz, $C_6D_6$): δ 0.75~2.38 (m, 31H), 1.10 (d, 2H, J=6.6 Hz), 2.14 (s; 6H), 2.70 (m, 2H,), 3.39 (q, 1H, J=6.9 Hz), 4.17 (m, 1H), 4.19 (m, 1H), 4.21 (m, 1H), 4.24 (s, 5H), 4.35 (m, 1H), 4.39 (m, 1H), 4.41 (m, 1H), 4.44 (m, 1H), 4.48 (m, 2H), 4.52 (1H), 4.80 (m, 1H). $^{31}$P NMR (121.5 MHz, $C_6D_6$): δ −21.4 (s), −7.9 (s)

$(R_C,S_{Fc},S_P)$-B16b: $^1$H NMR (300 MHz, $C_6D_6$): δ 0.94~2.40 (m, 32H), 1.30 (d, 2H, J=6.5 Hz), 2.63 (s, 6H), 2.72 (td, 1H, J=12.6 and 2.7 Hz), 3.93 (m, 1H), 4.08 (s, 5H), 4.21 (m, 1H), 4.28 (m, 1H), 4.38~4.47 (m, 7H), 4.51 (m, 1H), 4.72 (m, 1H). $^{31}$P NMR (121.5 MHz, $C_6D_6$): δ −26.9 (s), −8.4 (s).

EXAMPLE B17

Preparation of the Compound ($R_C,S_{FC},S_P$)-1-[2-(1-dimethylaminoethyl)ferrocen-1-yl]cyclohexylphosphino-1'-bis-[3,5-di(trifluoromethyl)phenyl]phosphinoferrocene (B17)

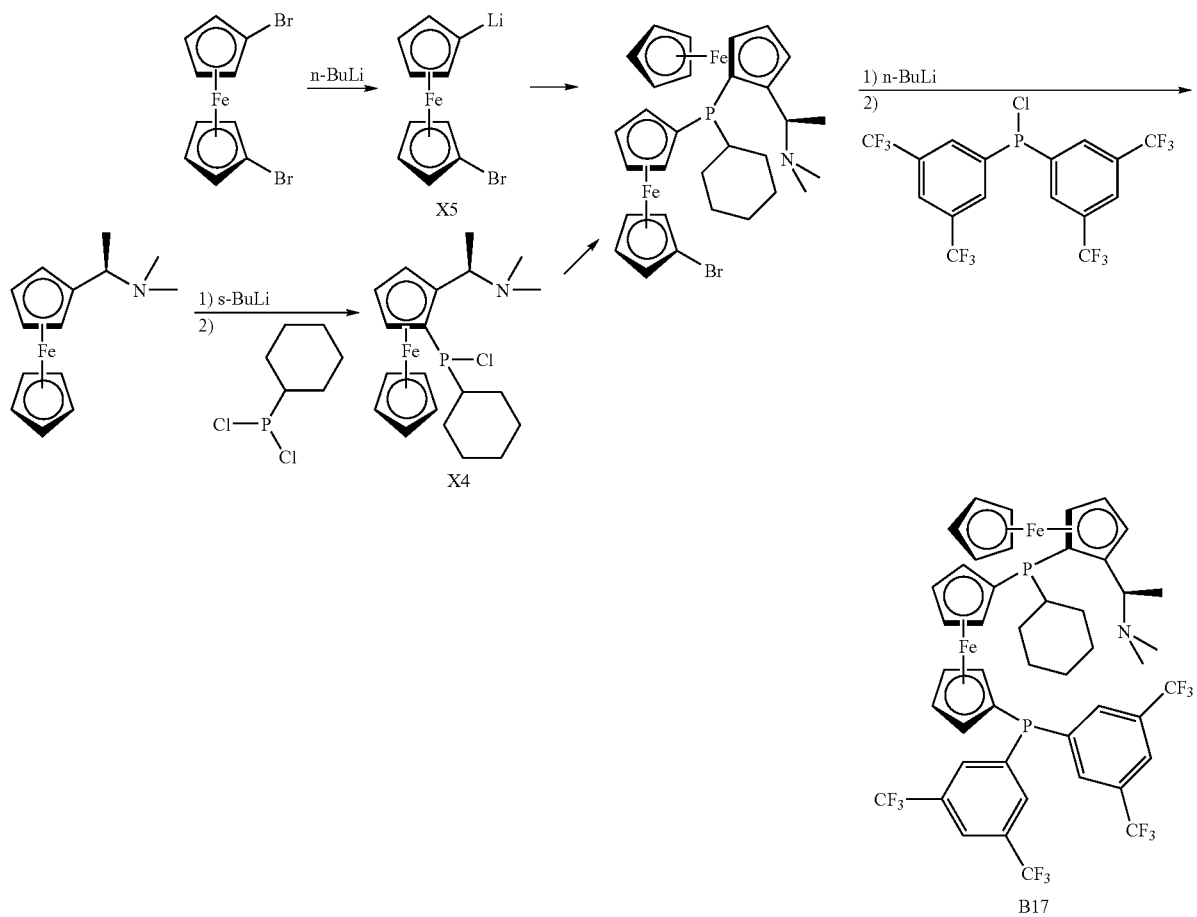

4 ml (10 mmol) of n-BuLi (2.5 M in hexane) are added dropwise to a solution of 3.44 g (10 mmol) of 1,1'-dibromoferrocene in 10 ml of tetrahydrofuran (THF) at a temperature of <−30° C. The mixture is stirred at this temperature for a further 1.5 hours to give a suspension of 1-bromo-1'-lithioferrocene X5.

In a second reaction vessel, 7.7 ml (10 mmol) of s-BuLi (1.3 M in cyclohexane) are added dropwise to a solution of 2.57 g (10 mmol) of (R)-1-dimethylamino-1-ferrocenylethane in 15 ml of TBME at <−10° C. After stirring the mixture at the same temperature for 10 minutes, the temperature is allowed to rise to 0° and the mixture is stirred for another 1.5 hours. The reaction mixture is then cooled to −78° C. and 1.51 ml (10 mmol) of dichlorocyclohexyl-phosphine are added. Further stirring at −78° C. for 30 minutes and, after removal of cooling, at room temperature for another one hour gives a suspension of the chlorophosphine X4 which is subsequently added at a temperature of <−10° C. to the suspension of 1-bromo-1'-lithioferrocene X5. The cooling is then removed and the mixture is stirred at room temperature for a further 1.5 hours. After renewed cooling to <−50° C., 4 ml (10 mmol) of n-BuLi (2.5 M in hexane) are added dropwise. After the addition, the temperature is allowed to rise to 0° C. and the mixture is stirred for a further 30 minutes. It is then cooled to −20° C. and 4.63 g (10 mmol) of bis[3,5-di(trifluoromethyl)phenyl]chlorophosphine are added. The cooling is subsequently removed and the mixture is stirred at room temperature for another 1.5 hours. The reaction mixture is admixed with 1N NaOH and extracted. The organic phase is dried over sodium sulphate and the solvent is distilled-off under reduced pressure on a rotary evaporator. The residue is subsequently heated at 150° C. for one hour. Chromatographic purification (silica gel 60; eluent=hexane/ethyl acetate 8:1) gives the compound B17 as a yellow solid (yield: 66%).

$^1$H NMR (300 MHz, $C_6D_6$): δ 1.25 (d, 3H, J=6.7 Hz), 1.00–2.29 (m, 11H), 2.20 (s, 6H), 3.78 (m, 1H), 4.02 (m, 1H), 4.04 (s, 5H), 4.09 (m, 1H), 4.14 (m, 1H), 4.17 (m, 1H), 4.21 (m, 1H), 4.40 (m, 2H), 4.60 (m, 1H), 7.80 (d, 2H, J=6.8 Hz), 8.00 (d, 4H, J=6.0 Hz). $^{31}$P NMR (121.5 MHz, $C_6D_6$): δ −27.1 (s); −14.1 (s).

EXAMPLES B18-B20

Description of Alternative Methods of Preparing the Diphosphine Ligands for the Example of the Compound $(R_C, S_{Fc}, S_P)$-1-[2-(1-dimethylaminoethyl)ferrocen-1-yl]phenylphosphino-1'-dicyclohexylphosphinoferrocene of the Formula (B1)

EXAMPLE B18

Reaction scheme

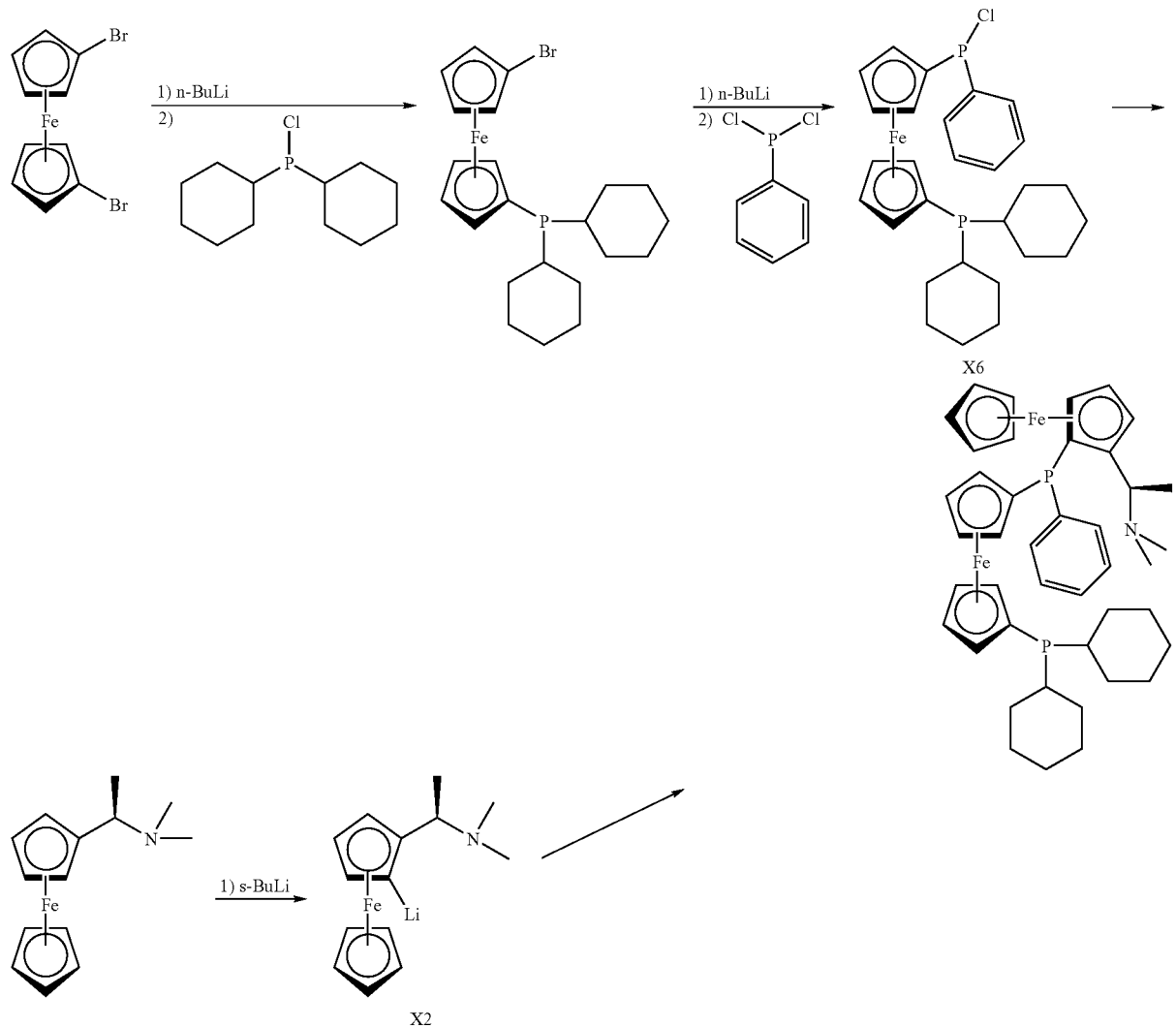

4 ml (10 mmol) of n-BuLi (2.5 M in hexane) are added dropwise to a solution of 3.44 g (10 mmol) of 1,1'-dibromoferrocene in 10 ml of tetrahydrofuran (THF) at a temperature of <−30° C. The mixture is stirred at this temperature for a further 1.5 hours. 2.21 ml (10 mmol) of dicyclohexylphosphine chloride are then added dropwise at such a rate that the temperature does not exceed −20° C. After stirring the mixture for a further 10 minutes, the temperature is allowed to rise to room temperature and the mixture is stirred for another one hour. It is cooled back down to 30° C. and 4.4 ml (11 mmol) of n-BuLi (2.5 M in hexane) are added dropwise. The mixture is subsequently stirred at −10° C. for 30 minutes. The reaction mixture is then cooled to −78° C. and 1.49 ml (11 mmol) of dichlorophenylphosphine are added. The mixture is stirred at −78° C. for 20 minutes and then at room temperature for a further one hour. This gives a reaction mixture comprising the monochlorodiphosphine X6.

In a second vessel, 8.5 ml (11 mmol) of s-BuLi (1.3 M in cyclohexane) are added dropwise to a solution of 2.57 g (10 mmol) of (R)-1-dimethylamino-1-ferrocenylethane in 15 ml of diethyl ether at <−10° C. After stirring the mixture at the same temperature for 10 minutes, the temperature is allowed to rise to 0° C. and the mixture is stirred for another 1.5 hours.

This reaction solution is subsequently added by means of a cannula to the reaction mixture comprising the monochlorodiphosphine X6 which has been cooled to −10° C. After the addition, the mixture is stirred at room temperature for another 2 hours. After addition of 10 ml of water, the reaction mixture is extracted, the organic phase is dried over sodium sulphate and the solvent is distilled off under reduced pressure on a rotary evaporator. The residue is heated at 140° C. for one hour. Column chromatography (silica gel 60; eluent: hexane/ethyl acetate 4:1) gives the compound of the formula (B1) in a yield of 47%. $^{31}$P- and $^{1}$H-NMR of the product are identical with those of Example B1.

EXAMPLE B19

Reaction scheme

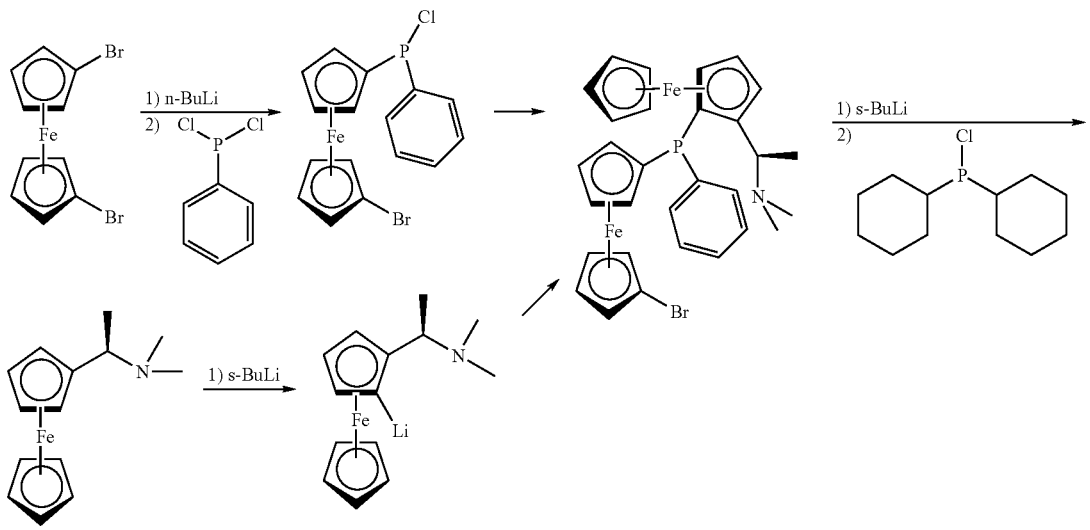

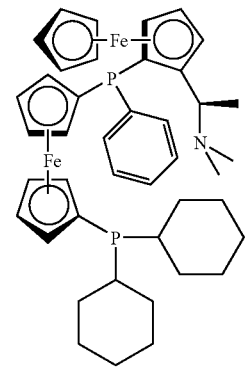

Reaction mixture 1: 4 ml (10 mmol) of n-BuLi (2.5 M in hexane) are added dropwise to a solution of 3.44 g (10 mmol) of 1,1'-dibromoferrocene in 10 ml of tetrahydrofuran (THF) at a temperature of <−30° C. The mixture is stirred at this temperature for a further 30 minutes. It is then cooled to −78° C. and 1.36 ml (10 mmol) of phenyldichlorophosphine are added. After stirring the mixture for a further 10 minutes, the temperature is allowed to rise to room temperature and the mixture is stirred for another one hour.

Reaction mixture 2: In a second vessel, 8.0 ml (0.4 mmol) of s-BuLi (1.3 M in cyclohexane) are added dropwise to a solution of 2.57 g (10 mmol) of (R)-1-dimethylamino-1-ferrocenyl-ethane in 15 ml of diethyl ether at <−10° C. After stirring the mixture at the same temperature for 10 minutes, the temperature is allowed to rise to 0° C. and the mixture is stirred for another 1.5 hours.

The reaction mixture 1 is slowly added to the reaction mixture 2 at a temperature below −10° C. The mixture is subsequently stirred at room temperature for 1.5 hours. At a temperature in the range from −78° C. to −50° C., 8 ml (10.4 mmol) of s-BuLi (1.3 M in cyclohexane) are then added dropwise. After stirring the mixture at −78° C. for 20 minutes, the temperature is allowed to rise to 0° C. and the mixture is stirred for a further 30 minutes before 2.21 ml (10 mmol) of chloro-dicyclohexylphosphine are added at −20° C. The mixture is stirred at 20° C. for another 20 minutes and finally at room temperature for another 1.5 hours. The work-up and thermal epimerization are carried out in a manner analogous to that described in Example B118. The compound of the formula (B1) is obtained in a yield of 31% $^{31}$P- and $^1$H-NMR of the product are identical with those of Example B1.

EXAMPLE B20

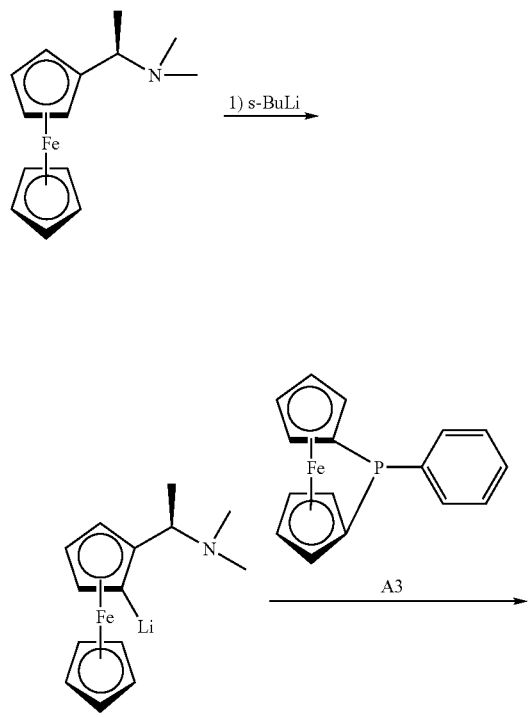

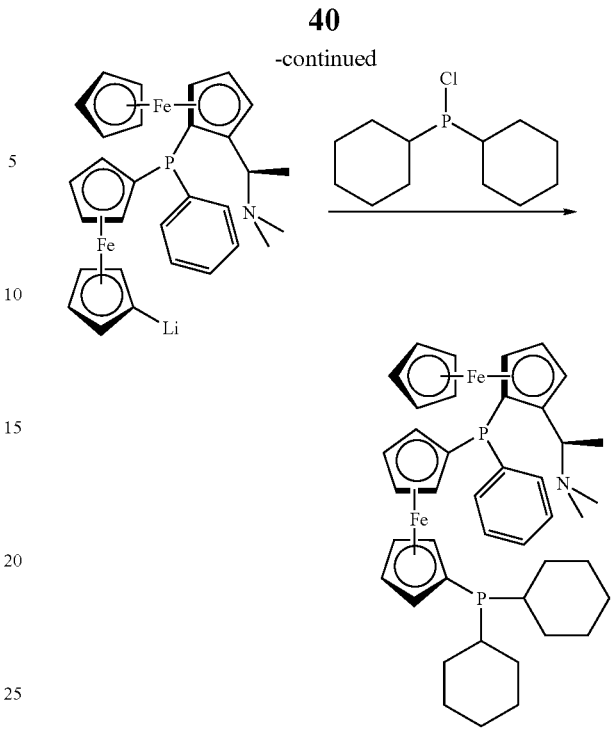

8.5 ml (11 mmol) of s-BuLi (1.3 M in cyclohexane) are added dropwise to a solution of 2.83 g (11 mmol) of (R)-1-dimethylamino-1-ferrocenylethane in 15 ml of diethyl ether at <−10° C. The cooling is then removed and the mixture is stirred at room temperature for another 2 hours. After cooling to −10° C., 2.92 g (10 mmol) of the compound A3 are added and the mixture is stirred at this temperature for a further 30 minutes. The temperature is allowed to rise to room temperature and the mixture is stirred for another one hour. After addition of 10 ml of 1N NaOH, the reaction mixture is extracted, the organic phase is dried over sodium sulphate and the solvent is distilled off under reduced pressure on a rotary evaporator. A $^1$H-NMR of the residue shows that the reaction is very stereoselective and gives virtually exclusively the desired diastereomer $(R_C, S_{Fc}, S_P)$-1-[2-(1-dimethylaminoethyl)ferrocen-1-yl]phenylphosphino-1'-dicyclohexylphosphinoferrocene. After chromatography (silica gel 60; eluent=hexane/ethyl acetate 4:1), this product is obtained in a yield of 37%. $^{31}$P and $^1$H-NMR of the product are identical to those of Example B1.

EXAMPLE B21

Preparation of the Compound $(R_C, S_{Fc}, S_P)$-1-[2-(1-methoxyethyl)ferrocen-1-yl]phenylphosphino-1'-dicyclohexylphosphinoferrocene of the Formula (B21)

The preparation is carried out in a manner analogous to that described in Example B18, except that (R)-1-methoxy-1-ferrocenylethane is used instead of (R)-1-dimethylamino-1-ferrocenylethane. The product B21 is purified by chromatography (silica gel 60: eluent hexane/ethyl acetate 4:1) and is obtained as an orange foam. $^1$H NMR (300 MHz, $C_6D_6$): δ 1.54 (d, 3H, J=6.4 Hz), 0.92-2.23 (m, 22H), 2.85 (s, 3H), 3.95 (m, 1H), 4.02 (m, 1H), 4.06 (m, 1H), 4.12 (m, 1H), 4.16 (s, 5H), 4.27 (m, 1H), (4.29 (m, 1H), 4.35 (m, 2H), 4.49 (m, 2H), 4.74 (m, 1H), 4.77 (m, 1H), 7.23 (m, 3H), 7.84 (m, 2H). $^{31}$P NMR (121.5 MHz, $C_6D_6$): δ −34.9 (s), −7.7 (s).

C) Preparation of Metal Complexes

EXAMPLE C1

Preparation of a Rhodium Complex (nbd is Norbornadiene)

11 mg (0.0148 mmol) of ligand B1 and 5.4 mg (0.0144 mmol) of [Rh(nbd)$_2$]BF$_4$ are dissolved in 0.8 ml of CD$_3$OD and stirred for 10 minutes. The solution is transferred to an NMR tube for measurement. $^{31}$P NMR (121.5 MHz, CD$_3$OD): Two superimposed doublets. Possible assignment: δ 26.60 (d, $J_{Rh-P}$=163 Hz), 26.30 (d, $J_{Rh-P}$=157 Hz).

D) Use Examples Hydrogenations

EXAMPLE D1-D29

Hydrogenation of

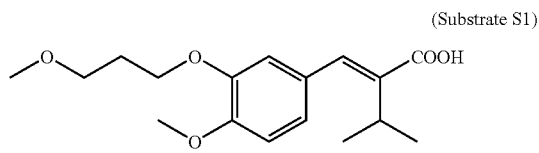

(Substrate S1)

EXAMPLE D1

Hydrogenation Using a Substrate/Catalyst Ratio (S/C) of 2000

3.04 mg (0.0041 mmol) of ligand B1 and 1.47 mg (0.0039 mmol) of [Rh(nbd)$_2$]BF$_4$ are weighed into a 25 ml Schlenk vessel provided with magnetic stirrer and rubber septum and dissolved in 2 ml of methanol. The solution is stirred for about 10 minutes. A solution of 2.4 g (7.783 mmol) of substrate S1 in 8 ml of methanol is then added. The resulting solution is transferred under pressure by means of a cannula into a 50 ml steel autoclave which is provided with heating and has previously been flooded with argon. The autoclave is connected via a reducing valve to a hydrogen reservoir. The autoclave is closed and the argon is replaced by hydrogen by two cycles of pressurization with hydrogen (60 bar) and depressurization. The autoclave is then pressurized again with 60 bar of hydrogen and the hydrogenation is started at 25° C. by switching on the stirrer. After 19.5 hours, the stirrer is switched off, the autoclave is depressurized and the hydrogenation solution is taken out. The conversion and the enantiomeric excess (ee) are determined by means of HPLC (Chirapak AD; 0.46×250 mm; hexane/EtOH/AcOH 950:50:1; flow=0.7 ml/minute; 20° C. The con-version is quantitative and the ee is 97.4% (S configuration).

The hydrogenations D2 to D25 and comparative examples Comp. 1 to Comp. 4 are carried out analogously at the temperatures and hydrogen pressures indicated in Table 2. In the case of hydrogenations having a relatively high S/C, less catalyst (0.85 mg (0.0023 mmol) of [Rh(nbd)$_2$]BF$_4$ and 0.0024 mmol of ligand) and more substrate are used. In all hydrogenations, the substrate concentration is 0.78 molar. An analogous procedure is used for the ligands B2 to B18 and B19 for comparison. The results are shown in Table 2.

TABLE 2

| Example | Ligand | S/C* | Addition | Temperature [° C.] | Pressure [bar] | Time [h] | Conversion (%) | ee | Configuration |
|---|---|---|---|---|---|---|---|---|---|
| D1 | B1 | 2000 | | 25 | 60 | 19.5 | 100 | 97.4 | S |
| D2 | B1 | 5000 | | 35 | 60 | 15.5 | 100 | 98.5 | S |
| D3 | B1 | 8500 | | 35 | 60 | 4 | 98 | 98.2 | S |
| D4 | B1 | 8500 | TFA° | 35 | 60 | 21 | 100 | 99.1 | S |
| D5 | B1 | 8500 | TFA° | 35 | 50 | 5 | 100 | 99.2 | S |
| D6 | B1 | 12000 | TFA° | 35 | 50 | 3.5 | 95 | 99.0 | S |
| D7 | B1 | 12000 | TFA° | 50 | 50 | 3.5 | 100 | 98.0 | S |
| D8 | B2 | 5000 | | 35 | 60 | 20.5 | 100 | 95.6 | S |
| D9 | B2 | 2000 | | 35 | 50 | 65 | 100 | 97.5 | S |
| D10 | B3 | 2000 | | 35 | 50 | 22 | 99 | 87.4 | S |
| D11 | B4 | 2000 | | 35 | 50 | 68 | 56 | 87.2 | S |
| D12 | B5 | 2000 | | 25 | 50 | 20 | 100 | 89.4 | S |
| D13 | B6 | 2000 | | 35 | 50 | 17 | 96 | 87.7 | S |
| D14 | B7 | 2000 | | 35 | 50 | 19 | 100 | 78.8 | S |
| D15 | B8 | 8500 | | 35 | 60 | 21 | 100 | 97.6 | S |
| D16 | B8 | 12000 | TFA° | 35 | 50 | 3.5 | 49.3 | 99.2 | S |
| D17 | B9 | 8500 | | 35 | 60 | 18 | 70 | 88.2 | S |
| D18 | B10 | 8500 | | 35 | 60 | 20 | 18 | 83.8 | S |
| D19 | B11 | 8500 | | 35 | 60 | 18 | 53 | 87 | S |
| D20 | B12 | 8500 | | 35 | 60 | 21 | 46 | 81.2 | S |
| D21 | B13 | 8500 | | 35 | 60 | 20 | 7 | 81.6 | S |
| D22 | B15b | 6700 | | 35 | 60 | 19 | 100 | 9.6 | S |
| D23 | B15a | 8500 | | 35 | 60 | 19 | 100 | 8.6 | R |
| D24 | B16b | 8500 | | 35 | 60 | 20 | 99 | 21.4 | S |
| D25 | B18 | 8500 | | 35 | 60 | 20 | 100 | 44 | S |
| Comp. 1 | B19 | 8500 | | 35 | 60 | 20 | 20 | 96.2 | S |
| Comp. 2 | B19 | 12000 | TFA° | 35 | 50 | 3.5 | 14 | 99.5 | S |
| Comp. 3 | B19 | 2000 | | 35 | 50 | 18.5 | 100 | 98.5 | S |
| Comp. 4 | B19 | 2000 | TFA° | 35 | 50 | 4 | 97 | 99.4 | S |

*S/C = Substrate/catalyst ratio;
°TFA = trifluoroacetic acid;

ligand B19 is 1,1'-bis[(S$_P$,R$_C$,S$_{Fe}$)(1-N,N-dimethylamino)ethylferrocenyl)phenylphosphino]ferrocene. It can be prepared as described in WO2006/075166, page 10, Example 1.

EXAMPLE D26-D27

Hydrogenation of

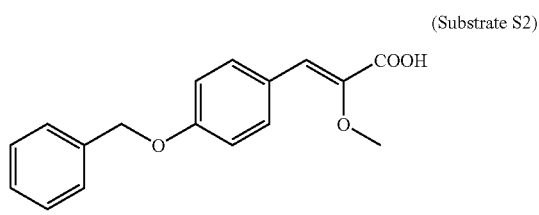
(Substrate S2)

1.87 mg (0.005 mmol) of [Rh(nbd)$_2$]BF$_4$ and 0.005 mmol of ligand are weighed into a 10 ml Schlenk vessel provided with magnetic stirrer and rubber septum and dissolved in 1 ml of methanol. The solution is stirred for 10 minutes and a solution of 143 mg (0.5 mmol) of substrate S2 in 4 ml of methanol (S/C=100) or 285 mg (1 mmol) in 9 ml (S/C=200) is then added. The resulting solution is transferred under pressure via a cannula to a 50 ml steel autoclave and hydrogenated in a manner analogous to that described in Example D1. The conversion and the enantiomeric excess (ee) are determined by means of HPLC (Chirapak. AD-H; 0.46×250 mm). The results are shown in Table 3.

TABLE 3

| Example | Ligand | S/C | Temperature [°C.] | Pressure [bar] | Time [h] | Conversion (%) | ee |
|---|---|---|---|---|---|---|---|
| D26 | B1 | 100 | 25 | 20 | 17 | 100 | 86.0 |
| D27 | B8 | 200 | 40 | 20 | 17 | 100 | 95.2 |

EXAMPLES D28-36

Hydrogenation of the Substrates S3, S4 and S5

(Substrate S3)

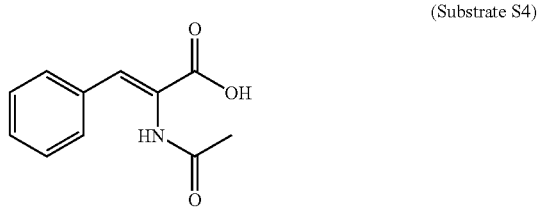
(Substrate S4)

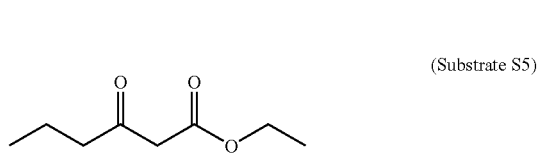
(Substrate S5)

The hydrogenations are carried out in 1.2 ml ampoules. Instead of stirring, intensive shaking is carried out. In a glove box, solutions having a volume of 0.5 ml and compositions shown in Table 4 are prepared in the 1.2 ml ampoules under a nitrogen atmosphere. The catalysts are prepared in situ by mixing 1 equivalent of [Rh(nbd)$_2$]BF$_4$ with 1.3 equivalents of ligand in dichloroethane and subsequently distilling off the dichloroethane under reduced pressure. The substrate is dissolved in the hydrogenation solvent and added as a solution to the catalyst. The ampoules are fixed in place in a pressure-rated, heatable container, the container is closed, the desired temperature is set, the nitrogen atmosphere in the container is replaced by a hydrogen atmosphere at the desired pressure and the hydrogenation is started by switching on the shaker. The conversion and the enantiomeric excess (ee) for the substrates S3 and S4 are determined by means of GC (Chrasil-L-val). The hydrogenation samples from substrate S4 are derivatized beforehand by means of TMS-diazomethane. The conversion and ee for substrate S5 are determined by means of GC (Lipodex-E). The results are summarized in Table 4.

TABLE 4

| Example | Ligand | Substrate | S/C* | Solvent | Temperature [°C.] | Pressure [bar] | Time [h] | Conversion (%) | ee |
|---|---|---|---|---|---|---|---|---|---|
| D28 | B1 | S3 | 100 | EtOH | 25 | 1 | 2 | 100 | 97 |
| D29 | B3 | S3 | 25 | EtOH | 25 | 1 | 2 | 100 | 94 |
| D30 | B9 | S3 | 100 | EtOH | 25 | 1 | 2 | 100 | 95 |
| D31 | B11 | S3 | 100 | EtOH | 25 | 1 | 2 | 100 | 94 |
| D32 | B14 | S3 | 100 | EtOH | 25 | 1 | 2 | 100 | 95 |
| D33 | B18 | S3 | 100 | EtOH | 25 | 1 | 2 | 100 | >99 |
| D34 | B1 | S4 | 25 | THF | 25 | 1 | 2 | 100 | 94 |
| D35 | B14 | S4 | 25 | THF | 25 | 1 | 2 | 100 | 97 |
| D36* | B3 | S5 | 100 | DCE | 80 | 80 | 14 | 100 | 79 |

*In this hydrogenation, [RuI$_2$(p-cymene)]$_2$ is used instead of [Rh(nbd)$_2$]BF$_4$.

EXAMPLE D37

Hydrogenation of Substrate S6

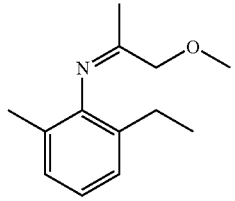

(Substrate S6)

4.89 mg (0.0067 mmol) of ligand B3 and 2.12 mg (0.0032 mmol) of [Ir(cod)Cl]$_2$ are weighed into a 25 ml Schlenk vessel provided with magnetic stirrer and rubber septum and dissolved in 2 ml of toluene. The solution is stirred for about 10 minutes. A solution of 260 mg (1.27 mmol) of substrate S6, 4.7 mg of tetrabutylammonium iodide and 30 mg of acetic acid in 3 ml of toluene is then added. The resulting solution is transferred under pressure via a cannula into a 50 ml steel autoclave provided with heating. The hydrogenation is carried out in a manner analogous to that described in Example D1 (hydrogenation time=19 hours; room temperature; hydrogen pressure=80 bar). The conversion and the enantiomeric excess (ee) are determined by means of HPLC (Chiracel OD-H). The conversion is quantitative and the ee is 31% (R configuration).

The invention claimed is:

1. A compound of the formula I in the form of an enantiomerically pure diastereomer or a mixture of diastereomers,

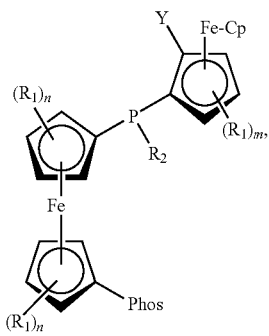

where the radicals R$_1$ are identical or different and are each C$_1$-C$_4$-alkyl;

m is 0 or an integer from 1 to 3;

n is 0 or an integer from 1 to 4;

R$_2$ is a hydrocarbon radical or a C-bonded heterohydrocarbon radical;

Cp is unsubstituted or C$_1$-C$_4$-alkyl-substituted cyclopentadienyl;

Y is —HC*R$_5$R$_6$ (wherein * denotes the asymmetric atom), wherein

R$_5$ is C$_1$-C$_8$-alkyl, C$_5$-C$_8$-cycloalkyl, C$_6$-C$_{10}$-aryl, C$_7$-C$_{12}$-aralkyl or C$_7$-C$_{12}$-alkaryl, R$_6$ is —OR$_7$ or —NR$_8$R$_9$, R$_7$ is C$_1$-C$_8$-alkyl, C$_5$-C$_8$-cycloalkyl, phenyl or benzyl and R$_8$ and R$_9$ are identical or different and are each C$_1$-C$_8$-alkyl, C$_5$-C$_8$-cycloalkyl, phenyl or benzyl or R$_8$ and R$_9$ together with the N atom form a five- to eight-membered ring; and Phos is a secondary phosphino group containing linear or branched C$_1$-C$_{12}$-alkyl; unsubstituted or C$_1$-C$_6$-alkyl- or C$_1$-C$_6$-alkoxy-substituted C$_5$-C$_{12}$-cycloalkyl or C$_5$-C$_{12}$-cycloalkyl-CH$_2$—; C$_6$-C$_{14}$-aryl; C$_4$-C$_{12}$-heteroaryl; C$_7$-C$_{14}$-aralkyl; C$_4$-C$_{12}$-heteroaralkyl; or halogen- (fluorine-, chlorine- or bromine-), C$_1$-C$_6$-alkyl-, trifluoromethyl-, C$_1$-C$_6$-alkoxy-, trifluoromethoxy-, (C$_6$H$_5$)$_3$Si—, (C$_1$-C$_{12}$-alkyl)$_3$Si— or sec-amino-substituted C$_6$-C$_{14}$-aryl, C$_4$-C$_{12}$-heteroaryl, C$_7$-C$_{14}$-aralkyl or C$_4$-C$_{12}$-heteroaralkyl and heteroaryl and heteroaralkyl contain heteroatoms selected from the group consisting of O, S and —N=.

2. A compound according to claim 1, wherein m and n are each 0.

3. A compound according to claim 1, wherein R$_2$ is an unsubstituted or substituted hydrocarbon radical which has from 1 to 22 carbon atoms and can contain heteroatoms selected from the group consisting of O, S, —N= or N(C$_1$-C$_4$-alkyl).

4. A compound according to claim 3, wherein R$_2$ is a radical selected from the group consisting of linear or branched C$_1$-C$_{12}$-alkyl; unsubstituted or C$_1$-C$_6$-alkyl- or C$_1$-C$_6$-alkoxy-substituted C$_5$-C$_{12}$-cycloalkyl or C$_5$-C$_{12}$-cycloalkyl-CH$_2$—; C$_6$-C$_{14}$-aryl; C$_4$-C$_{12}$-heteroaryl; C$_7$-C$_{14}$-aralkyl; C$_4$-C$_{12}$-heteroaralkyl; or halogen- (fluorine-, chlorine- or bromine-), C$_1$-C$_6$-alkyl-, trifluoromethyl-, C$_1$-C$_6$-alkoxy-, trifluoromethoxy-, (C$_6$H$_5$)$_3$Si—, (C$_1$-C$_{12}$-alkyl)$_3$Si— or sec-amino-substituted C$_6$-C$_{14}$-aryl, C$_4$-C$_{12}$-heteroaryl, C$_7$-C$_{14}$-aralkyl or C$_4$-C$_{12}$-heteroaralkyl, where heteroaryl and heteroaralkyl contain heteroatoms selected from the group consisting of O, S and —N=.

5. A compound according to claim 3, wherein R$_2$ is C$_1$-C$_6$-alkyl, C$_5$-C$_8$-cycloalkyl, C$_7$-C$_8$-bicycloalkyl, o-furyl, phenyl, naphthyl, 2-(C$_1$-C$_6$-alkyl)C$_6$H$_4$, 3-(C$_1$-C$_6$-alkyl) C$_6$H$_4$, 4-(C$_1$-C$_6$-alkyl)C$_6$H$_4$, 2-(C$_1$-C$_6$-alkoxy)C$_6$H$_4$, 3-(C$_1$-C$_6$-alkoxy)C$_6$H$_4$, 4-(C$_1$-C$_6$-alkoxy) C$_6$H$_4$, 2-(trifluoromethyl) C$_6$H$_4$, 3-(trifluoromethyl)C$_6$H$_4$, 4-(trifluoromethyl)C$_6$H$_4$, 3,5-bis(trifluoromethyl)C$_6$H$_3$, 3,5-bis(C$_1$-C$_6$-alkyl)$_2$C$_6$H$_3$, 3,5-bis(C$_1$-C$_6$-alkoxy)$_2$C$_6$H$_3$ and 3,5-bis(C$_1$-C$_6$-alkyl)$_2$-4-(C$_1$-C$_6$-alkoxy)C$_6$H$_2$.

6. A compound according to claim 1, wherein Y is a —CHR$_5$—NR$_8$R$_9$ group, where R$_5$ is C$_1$-C$_4$-alkyl, C$_5$-C$_6$-cycloalkyl, phenyl, C$_1$-C$_4$-alkylphenyl or C$_1$-C$_4$-alkylbenzyl and R$_8$ and R$_9$ are identical and are each C$_1$-C$_4$-alkyl.

7. A compound according to claim 1, wherein Y is 1-dimethylaminoeth-1-yl or (dimethylamino)phenyl-CH—.

8. A compound according to claim 1, wherein the secondary phosphino group is —P(C$_1$-C$_6$-alkyl)$_2$, —P(C$_5$-C$_8$-cycloalkyl)$_2$, —P(C$_7$-C$_8$-bicycloalkyl)$_2$, —P(o-furyl)$_2$, —P(C$_6$H$_5$)$_2$, —P(1-naphthyl)$_2$, —P[2-(C$_1$-C$_6$-alkyl)C$_6$H$_4$]$_2$, —P[3-(C$_1$-C$_6$-alkyl)C$_6$H$_4$]$_2$, —P[4-(C$_1$-C$_6$-alkyl)C$_6$H$_4$]$_2$, —P[2-(C$_1$-C$_6$-alkoxy)C$_6$H$_4$]$_2$, —P[3-(C$_1$-C$_6$-alkoxy)C$_6$H$_4$]$_2$, —P[4-(C$_1$-C$_6$-alkoxy)C$_6$H$_4$]$_2$, —P[2-(trifluoromethyl)C$_6$H$_4$]$_2$, —P[3-(trifluoromethyl)C$_6$H$_4$]$_2$, —P[4-(trifluoromethyl)C$_6$H$_4$]$_2$, —P[3,5-bis(trifluoromethyl)C$_6$H$_3$]$_2$, —P[3,5-bis(C$_1$-C$_6$-alkyl)$_2$C$_6$H$_3$]$_2$, —P[3,5-bis(C$_1$-C$_6$-alkoxy)$_2$ $C_6H_3]_2$ or $-P[3,5\text{-bis}(C_1\text{-}C_6\text{-alkyl})_2\text{-}4\text{-}(C_1\text{-}C_6\text{-alkoxy})C_6H_2]_2$ or a cyclic phosphino radical selected from the group consisting of

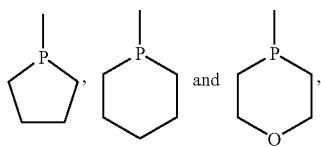

which are unsubstituted or substituted one or more times by $C_1$-$C_4$-alkyl, $C_1$-$C_4$-alkoxy, $C_1$-$C_4$-alkoxy-$C_1$-$C_2$-alkyl, phenyl, benzyl, benzyloxy or $C_1$-$C_4$-alkylidenedioxyl.

9. A process for preparing a compound of the formula I as defined in claim 1, which comprises the steps:
   a) metallation of a 1,1'-dihaloferrocene to give a 1-metallo-1'-haloferrocene and subsequent reaction with a compound of the formula $R_2$—$P(Hal)_2$, where Hal is chlorine, bromine or iodine, to form a compound of the formula VI,

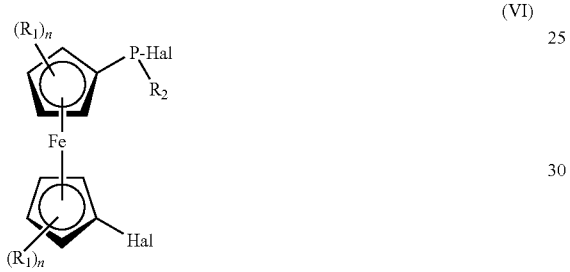

(VI)

wherein $R_1$, $R_2$ and n are as defined in claim 1,
   b) reaction of a compound of the formula VI with a compound of the formula VII

(VII)

where Y, Cp, $R_1$ and m are as defined in claim 1 and M is Li or MgHal, where Hal is chlorine, bromine or iodine, to form a compound of the formula VIII,

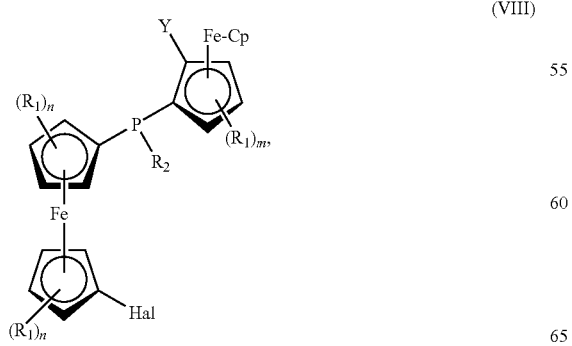

(VIII)

c) reaction of a compound of the formula VIII with an alkyllithium and then with a halophosphine of the formula Phos-Hal, where Hal is chlorine, bromine or iodine, to give a compound of the formula I.

10. A process according to claim 9, wherein the compound of the formula VIII is converted into essentially pure diastereomers by thermal treatment before process step c).

11. A compound of the formula VIII in the form of an enantiomerically pure diastereomer or a mixture of diastereomers,

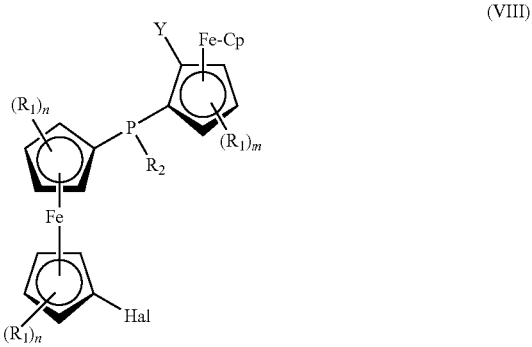

(VIII)

where the radicals $R_1$ are identical or different and are each $C_1$-$C_4$-alkyl;

m is 0 or an integer from 1 to 3;

n is 0 or an integer from 1 to 4;

$R_2$ is a hydrocarbon radical or C-bonded heterohydrocarbon radical;

Cp is unsubstituted or $C_1$-$C_4$-alkyl-substituted cyclopentadienyl;

Y is —HC*$R_5R_6$ (wherein * denotes the asymmetric atom), wherein $R_5$ is $C_1$-$C_8$-alkyl, $C_5$-$C_8$-cycloalkyl, $C_6$-$C_{10}$-aryl, $C_7$-$C_{12}$-aralkyl or $C_7$-$C_{12}$-alkaryl, $R_6$ is —$OR_7$ or —$NR_8R_9$, $R_7$ is $C_1$-$C_8$-alkyl, $C_5$-$C_8$-cycloalkyl, phenyl or benzyl and $R_8$ and $R_9$ are identical or different and are each $C_1$-$C_8$-alkyl, $C_5$-$C_8$-cycloalkyl, phenyl or benzyl or $R_8$ and $R_9$ together with the N atom form a five- to eight-membered ring; and Hal is chlorine, bromine or iodine.

12. A process for preparing a compound of the formula I as defined in claim 1, which comprises the steps:
   a) metallation of a 1,1'-dihaloferrocene to form a 1-metallo-1'-haloferrocene and subsequent reaction with a compound of the formula Phos-Hal, where halo and Hal are each chlorine, bromine or iodine, to form a compound of the formula IX

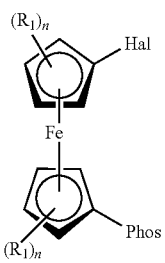
(IX)

where $R_1$, Phos and n are as defined in claim 1 and Hal is chlorine, bromine or iodine, b) metallation of the compound of the formula IX and subsequent reaction with a compound of the formula $R_2$—$P(Hal)_2$ to form a compound of the formula X,

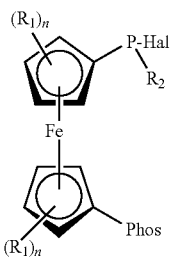
(X)

where $R_1$, $R_2$, Phos, Hal and n are as defined in claim 1 and Hal is chlorine, bromine or iodine, and c) reaction of a compound of the formula X with a compound of the formula VII

(VII)

where Y, Cp, $R_1$ and m are as defined in claim 1 and m is Li or MgHal, where Hal is chlorine, bromine or iodine, to give a compound of the formula I.

13. A process according to claim 12, wherein the compound of the formula I obtained in process step c) is converted into essentially a pure diastereomer by thermal treatment.

\* \* \* \* \*

UNITED STATES PATENT AND TRADEMARK OFFICE
CERTIFICATE OF CORRECTION

PATENT NO.         : 8,106,227 B2
APPLICATION NO.    : 12/226213
DATED              : January 31, 2012
INVENTOR(S)        : Wei-Ping Chen et al.

It is certified that error appears in the above-identified patent and that said Letters Patent is hereby corrected as shown below:

Title Page;
In section (73), "Solviasag" should be --Solvias AG--.

Signed and Sealed this
Twenty-sixth Day of June, 2012

David J. Kappos
*Director of the United States Patent and Trademark Office*